(12) United States Patent
Seitz et al.

(10) Patent No.: US 6,967,829 B2
(45) Date of Patent: Nov. 22, 2005

(54) CAPACITOR INTERCONNECT DESIGN

(75) Inventors: Keith W. Seitz, Niagara Falls, NY (US); Kenneth Talamine, Williamsville, NY (US); Laurie O'Connor, East Aurora, NY (US); Michael Streun, Orangeville (CA); Wayne Glidden, 5426 Brushy Meadows Dr., Fuquay-Varina, NC (US) 27526; Barry Muffoletto, Alden, NY (US)

(73) Assignees: Greatbatch, Inc., Clarence, NY (US); Wayne Glidden, Fuquay-Varina, NC (US)

( * ) Notice: Subject to any disclaimer, the term of this patent is extended or adjusted under 35 U.S.C. 154(b) by 30 days.

(21) Appl. No.: 11/046,165

(22) Filed: Jan. 28, 2005

(65) Prior Publication Data

US 2005/0162810 A1    Jul. 28, 2005

Related U.S. Application Data

(60) Provisional application No. 60/540,263, filed on Jan. 28, 2004, provisional application No. 60/540,264, filed on Jan. 28, 2004.

(51) Int. Cl.[7] .............................. H01G 5/38; H01G 2/10
(52) U.S. Cl. ..................... 361/522; 361/517; 29/25.03; 607/5
(58) Field of Search .......................... 361/301.3, 301.4, 361/306.1, 327, 517, 520, 531, 535–537; 29/25.03; 607/5

(56) References Cited

U.S. PATENT DOCUMENTS

| | | | |
|---|---|---|---|
| 3,976,922 A * | 8/1976 | Peck et al. ................... | 361/434 |
| 5,894,403 A | 4/1999 | Shah et al. | |
| 5,920,455 A | 7/1999 | Shah et al. | |
| 6,032,075 A | 2/2000 | Pignato et al. | |
| 6,099,600 A | 8/2000 | Yan et al. | |
| 6,184,160 B1 | 2/2001 | Yan et al. | |
| 6,219,222 B1 | 4/2001 | Shah et al. | |
| 6,224,985 B1 | 5/2001 | Shah et al. | |
| 6,243,605 B1 * | 6/2001 | Youker et al. ................. | 607/7 |
| 6,402,793 B1 | 6/2002 | Miltich et al. | |
| 6,468,605 B2 | 10/2002 | Shah et al. | |
| 6,648,928 B2 | 11/2003 | Nielsen et al. | |
| 6,687,117 B2 | 2/2004 | Liu et al. | |
| 6,687,118 B1 | 2/2004 | O'Phelan et al. | |
| 6,850,405 B1 * | 2/2005 | Mileham et al. ............ | 361/302 |
| 2003/0090857 A1 | 5/2003 | Liu et al. | |
| 2004/0120099 A1 | 6/2004 | Elliott et al. | |

* cited by examiner

Primary Examiner—Eric W. Thomas
(74) Attorney, Agent, or Firm—Michael F. Scalise

(57) ABSTRACT

Structures for serially connecting at least two capacitors together are described. Serially connecting capacitors together provides device manufactures, such as those selling implantable medical devices, with broad flexibility in terms of both how many capacitors are incorporated in the device and what configuration the capacitor assembly will assume.

20 Claims, 19 Drawing Sheets

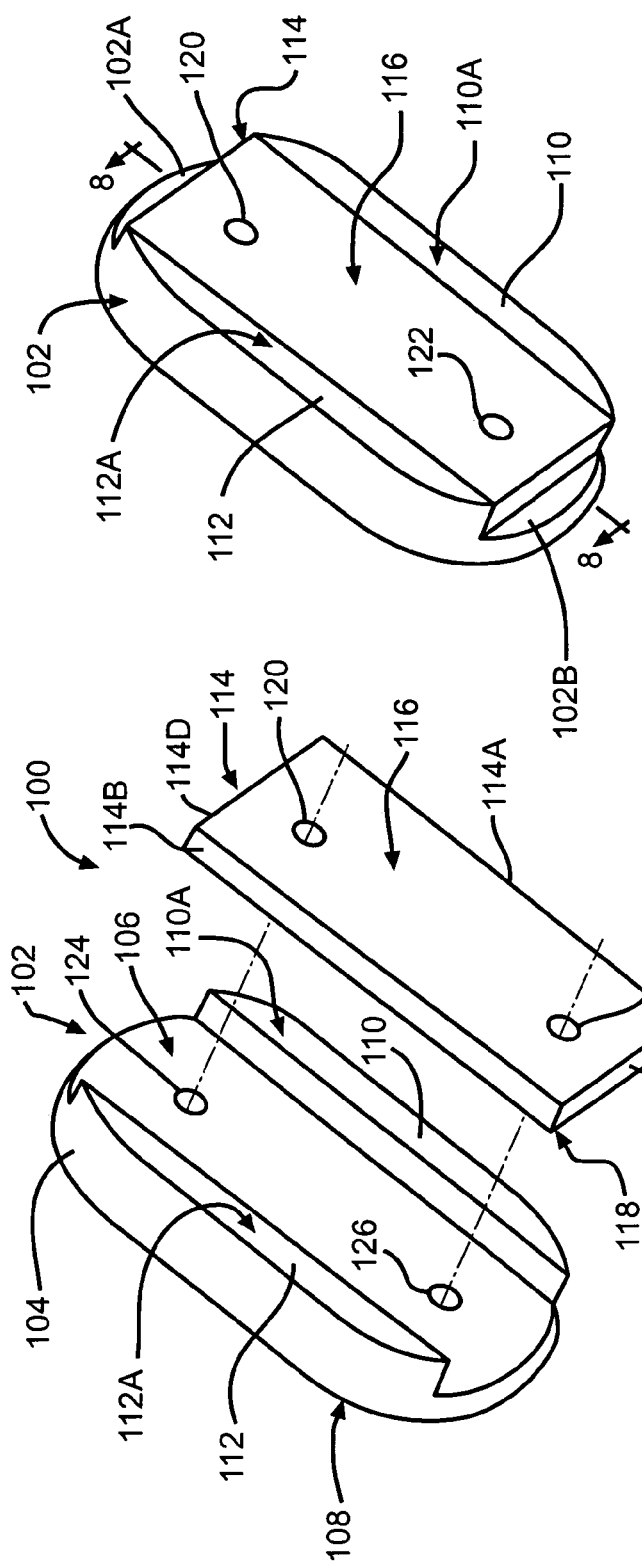
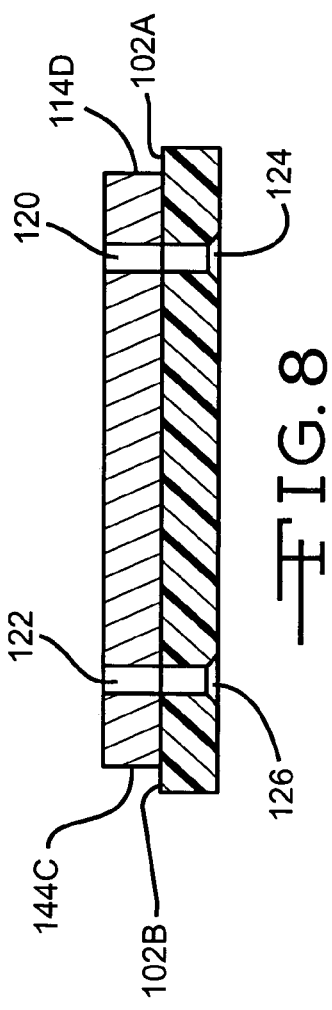

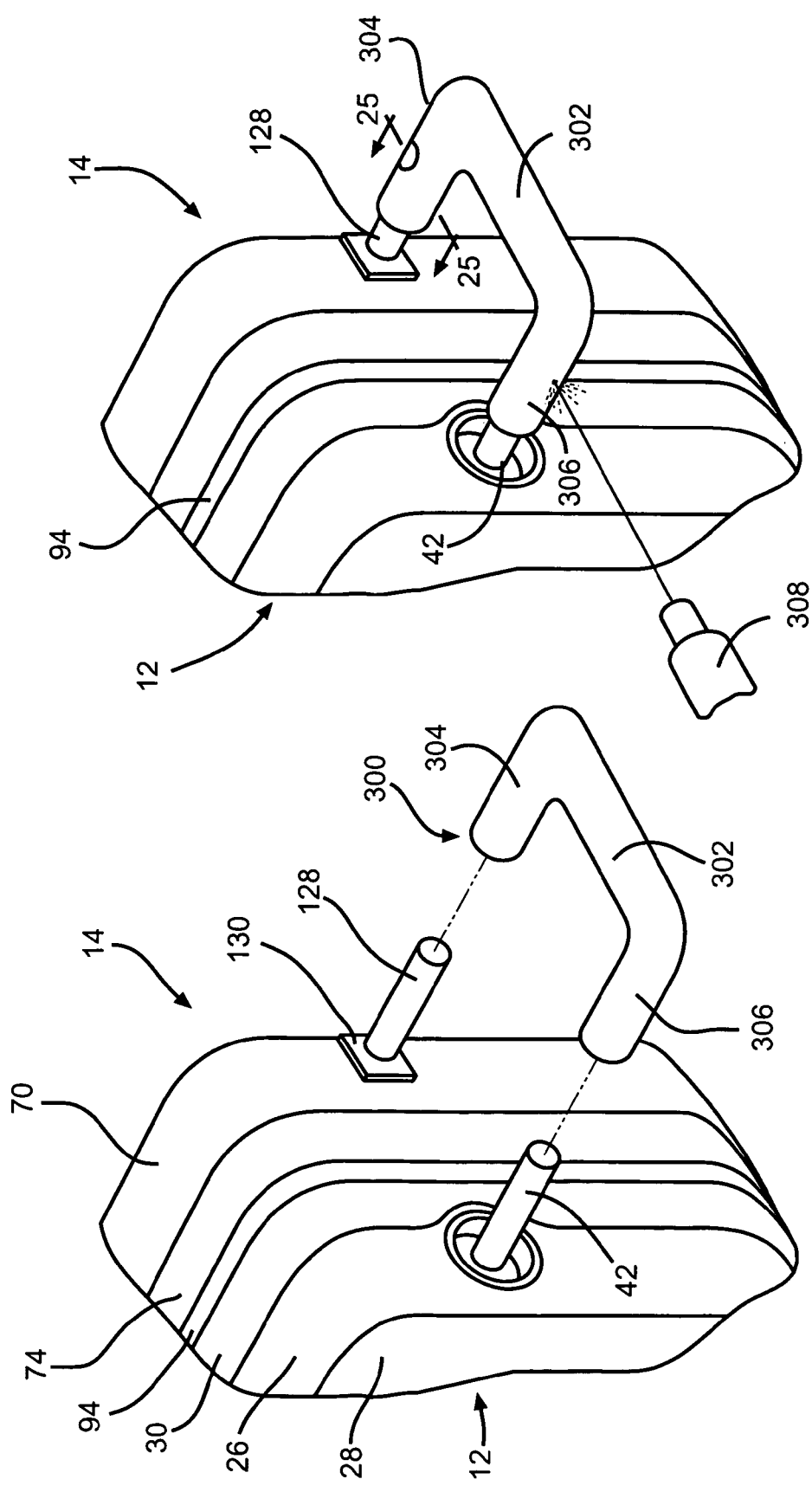

CAPACITOR INTERCONNECT DESIGN

CROSS-REFERENCE TO RELATED APPLICATIONS

The present application claims priority based upon provisional application Ser. Nos. 60/540,263 and 60/540,264, both filed Jan. 28, 2004.

BACKGROUND OF THE INVENTION

1. Field of the Invention

The present invention generally relates to a capacitor and, more particularly, to at least two side-by-side capacitors connected in series. This is done using various interconnect structures connecting between the negative polarity pin/casing of one capacitor to the positive polarity lead of another. The present interconnects are of a relatively low profile having a conductive member insulted from the capacitor casings and to which the positive pin and negative lead are welded. A polymeric material disposed there between otherwise insulates the side-by-side capacitors from each other.

2. Prior Art

FIGS. 1 to 4 show a conventional design for a series connected capacitor assembly 10 comprising a first capacitor 12 and a side-by-side second capacitor 14. The first capacitor 12 comprises an anode of an anode active material 16 and a cathode of a cathode active material 18 (FIG. 4) housed inside a hermetically sealed casing 20. The capacitor electrodes are operatively associated with each other by an electrolyte (not shown) contained inside the casing, as will be described in detail hereinafter. It should be pointed out that the capacitors 12, 14 can be of either an electrochemical type wherein both the anode and the cathode electrodes are provided by conductive substrates having a capacitive material contacted thereto, or an electrolyte type wherein the cathode electrode is provided by a conductive substrate having capacitive properties. The illustrated capacitors are preferably of the latter type, however, that should not be construed as limiting.

As particularly shown in FIGS. 2 and 3, casing 20 is of a metal material comprising mating first and second clamshells or mating casing portions 22 and 24. Casing portion 22 comprises a surrounding sidewall 26 extending to a face wall 28. Similarly, casing portion 24 comprises a surrounding sidewall 30 extending to a face wall 32. The sidewall 26 of the first casing portion 22 is sized to fit inside the periphery of the second sidewall 30 in a closely spaced relationship. This means that the first face wall 28 is somewhat smaller in planar area than the second face wall 32 of casing portion 24. Also, the height of the second surrounding sidewall 30 of casing portion 24 is less than the height of the first surrounding sidewall 26. The surrounding sidewall 26 has an inwardly angled lead-in portion 34 that facilitates mating the casing portions 22, 24 to each other.

With the first and second casing portions 22, 24 mated to each other, the distal end of the second surrounding sidewall 30 contacts the first surrounding sidewall 26 a short distance toward the face 28 from the bend forming the lead-in portion 34. The casing portions 22, 24 are hermetically sealed to each other by welding the sidewalls 26, 30 together at this contact location. The weld is provided by any conventional means; however, a preferred method is by laser welding.

The anode active material 16 is typically of a metal selected from the group consisting of tantalum, aluminum, titanium, niobium, zirconium, hafnium, tungsten, molybdenum, vanadium, silicon, germanium, and mixtures thereof in the form of a pellet. As is well known by those skilled in the art, the anode metal in powdered form, for example tantalum powder, is compressed into a pellet having an anode wire 36 embedded therein and extending there from, and sintered under a vacuum at high temperatures. The porous body is then anodized in a suitable electrolyte to fill its pores with the electrolyte and form a continuous dielectric oxide film on the sintered body. The assembly is then reformed to a desired voltage to produce an oxide layer over the sintered body and anode wire. The anode can also be of an etched aluminum or titanium foil.

The cathode electrode is spaced from the anode electrode housed inside the casing and comprises the cathode active material 18. The cathode active material has a thickness of about a few hundred Angstroms to about 0.1 millimeters directly coated on the inner surface of the face walls 28, 32 (FIGS. 2 to 4) or, it is coated on a conductive substrate (not shown) in electrical contact with the inner surface of the face walls. In that respect, the face walls 28, 32 may be of an anodized-etched conductive material, have a sintered active material with or without oxide contacted thereto, contacted with a double layer capacitive material, for example a finely divided carbonaceous material such as graphite or carbon or platinum black, a redox, pseudocapacitive or an under potential material, or be an electroactive conducting polymer such as polyaniline, polypyrol, polythiophene, and polyacetylene, and mixtures thereof.

The redox or cathode active material 18 includes an oxide of a first metal, a nitride of the first metal, a carbonnitride of the first metal, and/or a carbide of the first metal, the oxide, nitride, carbonnitride and carbide of the first metal having pseudocapacitive properties. The first metal is preferably selected from the group consisting of ruthenium, cobalt, manganese, molybdenum, tungsten, tantalum, iron, niobium, iridium, titanium, zirconium, hafnium, rhodium, vanadium, osmium, palladium, platinum, nickel, and lead, an oxide of the former being preferred.

The cathode active material 18 may also include a second or more metals. The second metal is in the form of an oxide, a nitride, a carbonnitride or carbide, and is not essential to the proper functioning of the capacitor electrode. The second metal is different than the first metal and is selected from one or more of the group consisting of tantalum, titanium, nickel, iridium, platinum, palladium, gold, silver, cobalt, molybdenum, ruthenium, manganese, tungsten, iron, zirconium, hafnium, rhodium, vanadium, osmium, and niobium.

The mating casing portions 22, 24, and the electrically connected conductive substrate if it is provided, are preferably selected from the group consisting of tantalum, titanium, nickel, molybdenum, niobium, cobalt, stainless steel, tungsten, platinum, palladium, gold, silver, copper, chromium, vanadium, aluminum, zirconium, hafnium, zinc, iron, and mixtures and alloys thereof. Preferably, the face and sidewalls of the casing portions have a thickness of about 0.001 to about 2 millimeters.

The exemplary electrolytic type capacitor shown in FIGS. 1 to 4 has the cathode active material 18 preferably coating the face walls 28, 32 spaced from the respective sidewalls 26, 30. Such a coating is accomplished by providing the conductive face walls 28, 32 with a masking material in a known manner so that only an intended area of the face walls is contacted with active material. The masking material is removed from the face walls prior to capacitor fabrication. Preferably, the cathode active material 18 is substantially aligned in a face-to-face relationship with the major faces of the anode active material 16. A preferred coating process is in the form of an ultrasonically generated aerosol as described in U.S. Pat. Nos. 5,894,403; 5,920,455; 6,224,985; and 6,468,605, all to Shah et al. These patents are assigned to the assignee of the present invention and incorporated herein by reference.

A separator (not shown) of electrically insulative material is provided between the anode active material 16 and the cathode active material 18 to prevent an internal electrical short circuit between them. The separator material also is chemically unreactive with the anode and cathode active materials and both chemically unreactive with and insoluble in the electrolyte. In addition, the separator material has a degree of porosity sufficient to allow flow therethrough of the electrolyte during the electrochemical reaction of the capacitor 12. Illustrative separator materials include woven and non-woven fabrics of polyolefinic fibers including polypropylene and polyethylene or fluoropolymeric fibers including polyvinylidene fluoride, polyethylenetetrafluoroethylene, and polyethylenechlorotrifluoroethylene laminated or superposed with a polyolefinic or fluoropolymeric microporous film, non-woven glass, glass fiber materials and ceramic materials. Suitable microporous films include a polyethylene membrane commercially available under the designation SOLUPOR® (DMS Solutech), a polytetrafluoroethylene membrane commercially available under the designation ZITEX® (Chemplast Inc.), a polypropylene membrane commercially available under the designation CELGARD® (Celanese Plastic Company, Inc.), and a membrane commercially available under the designation DEXIGLAS® (C. H. Dexter, Div., Dexter Corp.). Cellulose based separators typically used in capacitors are also contemplated. Depending on the electrolyte used, the separator can be treated to improve its wettability, as is well known by those skilled in the art.

A suitable electrolyte for the capacitors 12, 14 is described in U.S. Pat. No. 6,219,222 to Shah et al., which includes a mixed solvent of water and ethylene glycol having an ammonium salt dissolved therein. Other electrolytes for the present capacitors are described in U.S. Pat. No. 6,687,117 to Liu et al. and U.S. Pub. No. 2003/0090857. The electrolyte of the former patent comprises de-ionized water, an organic solvent, isobutyric acid and a concentrated ammonium salt while the latter publication relates to an electrolyte having water, a water-soluble inorganic or organic acid or salt, and a water-soluble nitro-aromatic compound. These patents and publication are assigned to the assignee of the present invention and incorporated herein by reference. The electrolyte is provided inside the hermetically sealed casing through a fill opening closed by a hermetic closure 38 (FIG. 1), as is well known by those skilled in the art.

The casing 20, including the portions 22, 24, being of a conductive metal serves as one terminal for making electrical connection between the capacitor and its load. A pin 40 (FIG. 2) is welded to the sidewall 26 to provide the negative terminal for the first capacitor 12. Pin 40 also provides the negative terminal for the side-by-side capacitor assembly 10, as will be described in detail hereinafter. The other electrical terminal or contact for the first capacitor 12 comprises the anode wire 36 extending from the anode active material 16 and connected to the anode lead 42 extending through the first surrounding sidewall 26.

As shown in FIGS. 2 and 3, the anode lead 42 is electrically insulated from the metal casing 20 by an insulator glass-to-metal feedthrough 46. The glass-to-metal feedthrough 46 comprises a ferrule 48 defining an internal cylindrical through bore or passage 50 of constant inside diameter. Outwardly facing annular steps 52A and 52B are provided at the respective upper and lower ferrule ends. The upper step 52A is of an outer diameter sized to fit in a closely spaced relationship in an annular opening 54 in the first casing sidewall 26 with the remaining body of the ferrule butted against the inner surface of the sidewall. The ferrule 48 is secured therein by welding, and the like.

As shown in FIG. 2, the anode active material 16 has a notch 56 that provides clearance for the glass-to-metal feedthrough 46. The anode wire 36 embedded in the anode active material 16 extends outwardly from the notch 56. A distal end 36A is bent into a position generally parallel to the longitudinal axis of ferrule 48. A proximal end 42A of the anode lead 42 is bent into a J-hook shape to align parallel with the distal end 36A of the anode wire 36. The distal end 36A of the anode wire is then welded to the proximal end 42A of the anode lead to electrically connect the anode to the lead 42.

An insulative glass 58 provides a hermetic seal between the inside of the ferrule 48 and the anode lead 42. The glass is, for example, ELAN® type 88 or MANSOL™ type 88. The anode lead 42 preferably comprises the same material as the anode active material 16. In that manner, the portion of the anode lead 42 extending outside the capacitor 12 for connection to a load is hermetically sealed from the interior of the capacitor and insulated from the mating casing portions 22, 24 serving as the terminal for the cathode.

The second capacitor 14 illustrated in drawing FIGS. 1 to 4 is similar to the first capacitor 12 in terms of its physical structure as well as its chemistry. As previously discussed, however, the capacitors 12, 14 need not be chemically similar. For example, the first capacitor 12 can be of an electrolytic type while the second capacitor 14 can be of the electrochemical type. Preferably, the capacitors 12, 14 are both of the electrolytic type.

The second capacitor 14 comprises an anode active material 60 and a cathode active material 62 (FIG. 3) housed inside a hermetically sealed casing 64 and operatively associated with each other by an electrolyte (not shown). Casing 64 is similar to casing 20 of capacitor 12 and comprises mating third and fourth portions 66 and 68 (FIG. 1). Casing portion 66 comprises a surrounding sidewall 70 extending to a face wall 72. Similarly, casing portion 68 comprises a surrounding sidewall 74 extending to a face wall 76. The sidewall 70 of the third casing portion 66 is sized to fit inside the periphery of the fourth sidewall 74 in a closely spaced relationship. The height of the fourth surrounding sidewall 74 is less than that of the third surrounding sidewall 70 and its inwardly angled lead-in portion 78. Laser welding the contacting sidewalls 70, 74 together hermetically seals the third and fourth mated casing portions 66, 68 to each other.

The cathode active material 62 is supported on the inner surfaces of the face walls 72, 76 opposite the major faces of the anode active material 60. In that manner, the casing 64, being of a conductive metal, serves as one terminal for making electrical connection between the capacitor 14 and its load.

The other electrical terminal or contact is provided by a conductor or lead 80 extending from within the capacitor 14 connected to the anode active material 60 and through the third surrounding sidewall 70. The anode active material 60 is similar in construction to the anode of capacitor 12 and includes a notch that provides clearance for a glass-to-metal feedthrough 82. An anode wire 84 embedded in the anode active material 60 extends outwardly from the notch to a distal end welded to the proximal end of the anode lead 80 to electrically connect the anode to the lead.

The glass-to-metal feedthrough 82 electrically insulates the anode lead 80 from the metal casing 64 and comprises a ferrule 86 provided with an annular step of reduced diameter fitted in a closely spaced relationship in an annular opening in the first casing sidewall 70. The remaining ferrule body is butted against the inner surface of the sidewall with the ferrule 86 being secured therein by welding. An insulative glass 88 hermetically seals between the cylindrical inner surface of the ferrule 86 and the anode lead 80.

A separator (not shown) of electrically insulative and ionically conductive material segregates the anode active material 60 from the cathode active material 62. The electrolyte is provided inside the hermetically sealed casing 64 through a fill opening closed by a hermetic closure 90.

The thusly constructed first and second capacitors 12, 14 are then positioned back-to-back or side-by-side. In this configuration, the face wall 32 of the casing portion 24 of the first capacitor 12 is aligned with and proximate to the face wall 76 of the casing portion 68 of the second capacitor 14. An adhesive 94 (FIG. 3), for example, a double-sided polyimide tape, secures the capacitors 12, 14 together without the respective casing portions 24, 68 being electrically shorted to each other. A suitable tape for this purpose is commercially available from E. I. Du Pont De Nemours and Company Corporation under the trademark KAPTON®. If desired, the capacitors 12, 14 are provided with a paralyene coating by a vacuum deposition process about their entire outer surface prior to being aligned in the side-by-side orientation.

The capacitors 12, 14 are then electrically connected in series. The prior art design used with the capacitors 12, 14 comprises a connecting tab 96 having a foot portion 96A secured to the surrounding sidewall 70 of casing portion 68, such as by welding, adjacent to the anode lead 42 for the first capacitor 12. An arm portion 96B of the tab is butted to the distal end of the anode lead 42. A weld (not shown) then finishes the connection of the tab 96 to the anode lead 42. This results in the positive polarity anode lead 42 of the first capacitor 12 being connected to the negative polarity casing 64 of the second capacitor 14. The series connected side-by-side capacitors 12, 14 are then connectable to a load (not shown). Connecting the negative polarity terminal pin 40 of the first capacitor 12 and the polarity terminal lead 80 of the second capacitor 14 does this.

While the prior art design works well, there are improvements that can be made to it. For one, the connection between the anode lead 42 and tab 96 is a "blind" butt weld that demonstrates very poor manufacturing yields. The lead 42 under the tab 96 is typically about 0.0013 to 0.0014 inches in diameter. The spot size for the laser welder is about 0.018 inches in diameter. This means that the laser needs to be aligned perfectly with the lead 42 to effect a robust connection. If not, the laser will blow through the tab 96, creating scrap. Welding the foot portion 96A of the tab 96 to the sidewall 70 of casing portion 68 and the arm portion 96B to the lead 42 are relatively slow processes that utilize expensive tooling to position the tab and then bend it into contact with the sleeve. Finally, the tab 96 can create a sharp edge and the butt-welded tab 96 and lead 42 interconnect takes up a relatively large amount of real estate in both the vertical direction off of the capacitors 12, 14 as well as laterally on the capacitor. The prior art connecting tab 96 and anode lead 42 design is the subject of U.S. Patent Application Pub. No. 2004/0120099. This application is assigned to the assignee of the present invention and incorporated herein by reference.

SUMMARY OF THE INVENTION

The current trend in medicine is to make cardiac defibrillators, and other implantable medical devices such as cardiac pacemakers, neurostimulators, and drug pumps, as small and lightweight as possible without compromising power. This, in turn, means that capacitors contained in these devices must be readily adaptable in how they are connected to each other as well as to the battery and the device circuitry. In that light, the present invention relates to structures for serially connecting at least two capacitors together to provide the device manufacture with broad flexibility in terms of both how many capacitors are incorporated in the device and what configuration the capacitor assembly will assume.

These and other aspects of the present invention will become more apparent to those skilled in the art by reference to the following description and to the appended drawings.

BRIEF DESCRIPTION OF THE DRAWINGS

FIG. 6 is an exploded view of the interconnect 100 shown in FIG. 5 including a platform 102 and a conductive bar 114.

FIG. 7 is a perspective view of the assembled interconnect 100 shown in FIG. 6.

FIG. 8 is a cross-sectional view along line 8—8 of FIG. 7.

FIG. 18A is a perspective view of a modified platform 202A provided with a cutout 214A.

FIG. 18B is a perspective view of the conductive bar 220 nested in the platform 202A shown in FIG. 18A to expose a edge 220A of the bar for wire bond connection to the series capacitors 12, 14.

FIG. 23 is a partial perspective view of another embodiment of an interconnect 300 being moved onto the terminals 42 and 128 for the capacitors 12, 14.

FIG. 24 is a partial perspective view of the interconnect 300 of FIG. 22 being welded to the terminals 42 and 128.

DETAILED DESCRIPTION OF THE PREFERRED EMBODIMENTS

Figure 1:
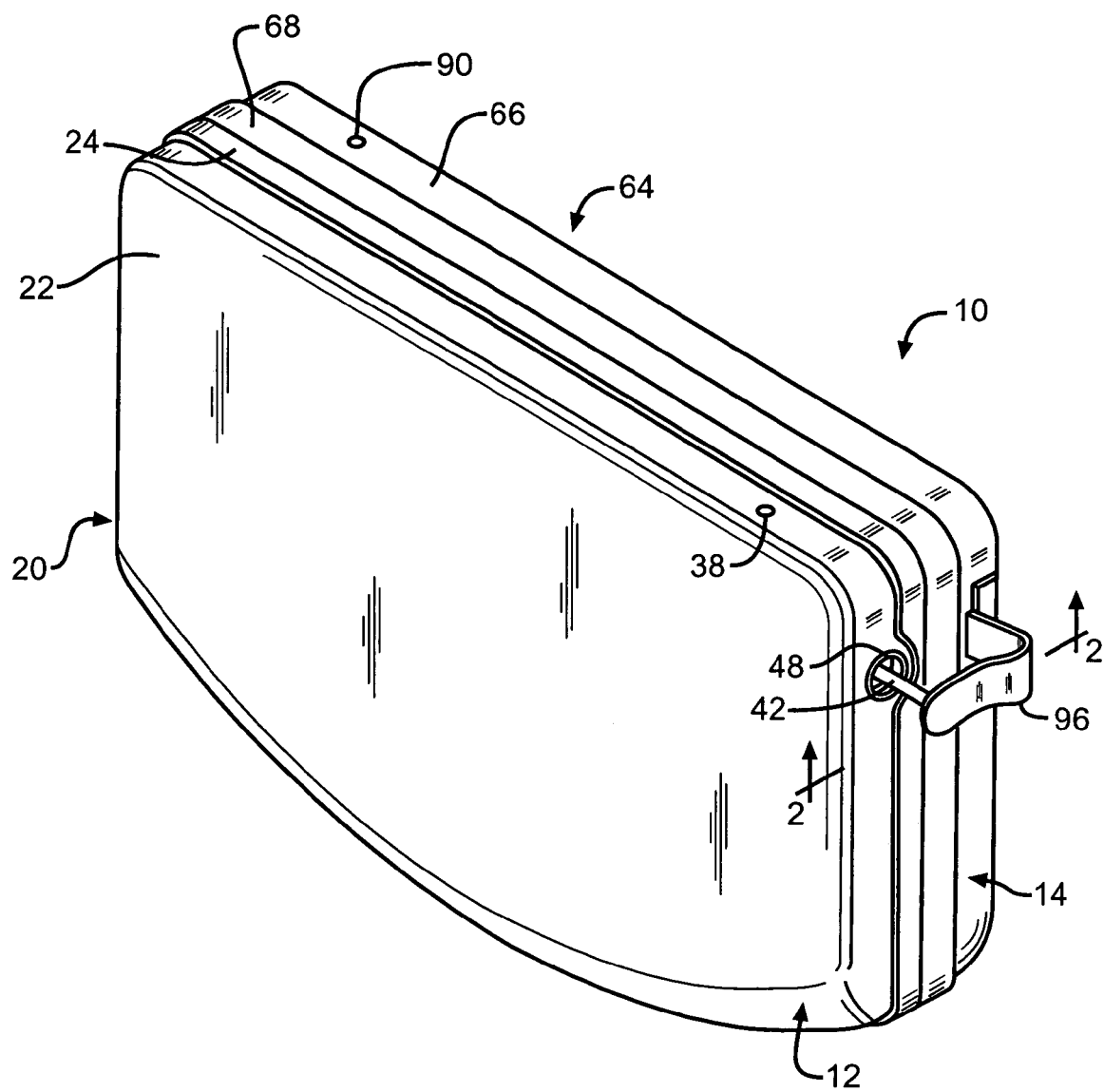
FIG. 1 is a perspective view looking at the right edges of two side-by-side capacitors 12, 14 connected in series according to the prior art.
Figure 2:
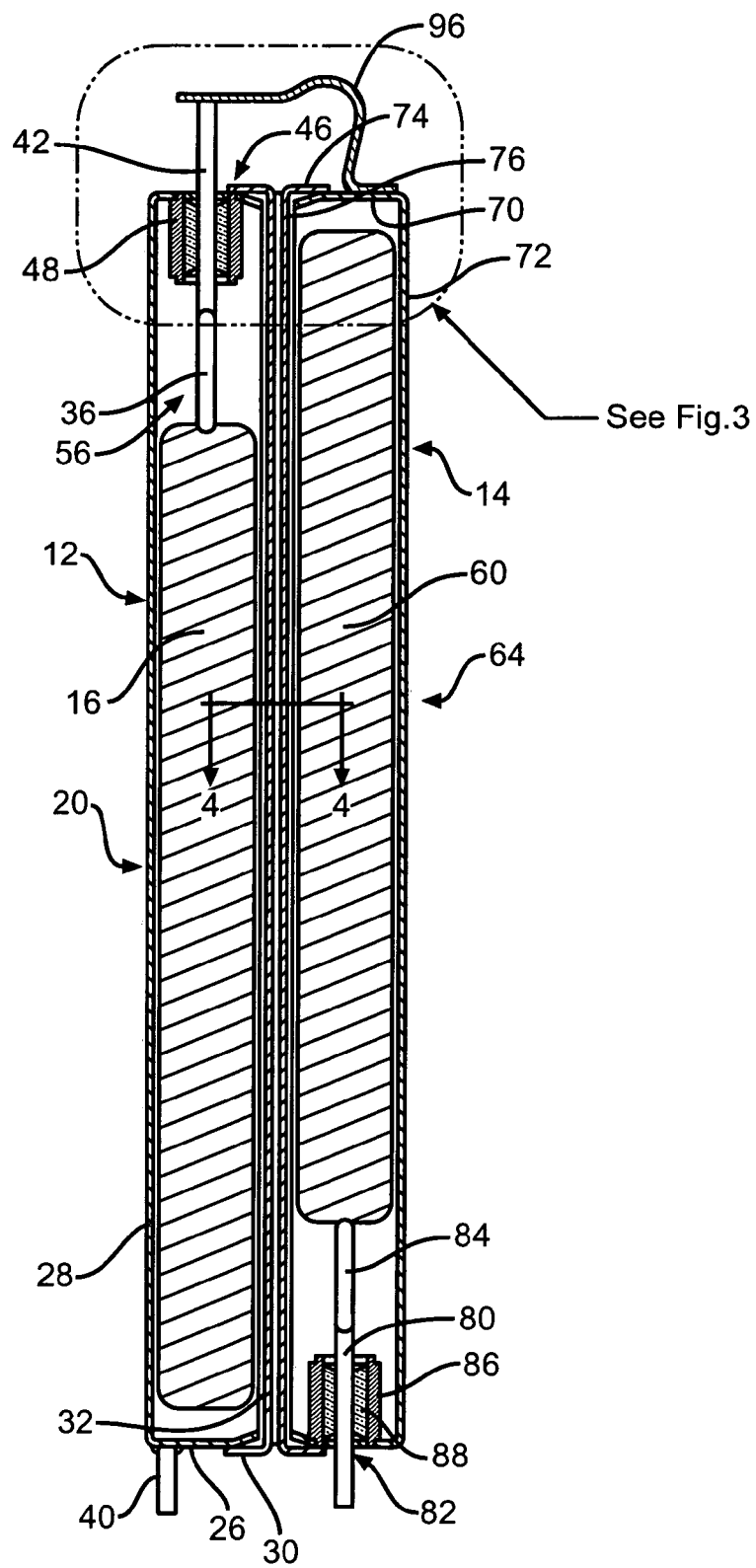
FIG. 2 is a cross-sectional view taken along line 2—2 of FIG. 1.
Figure 3:
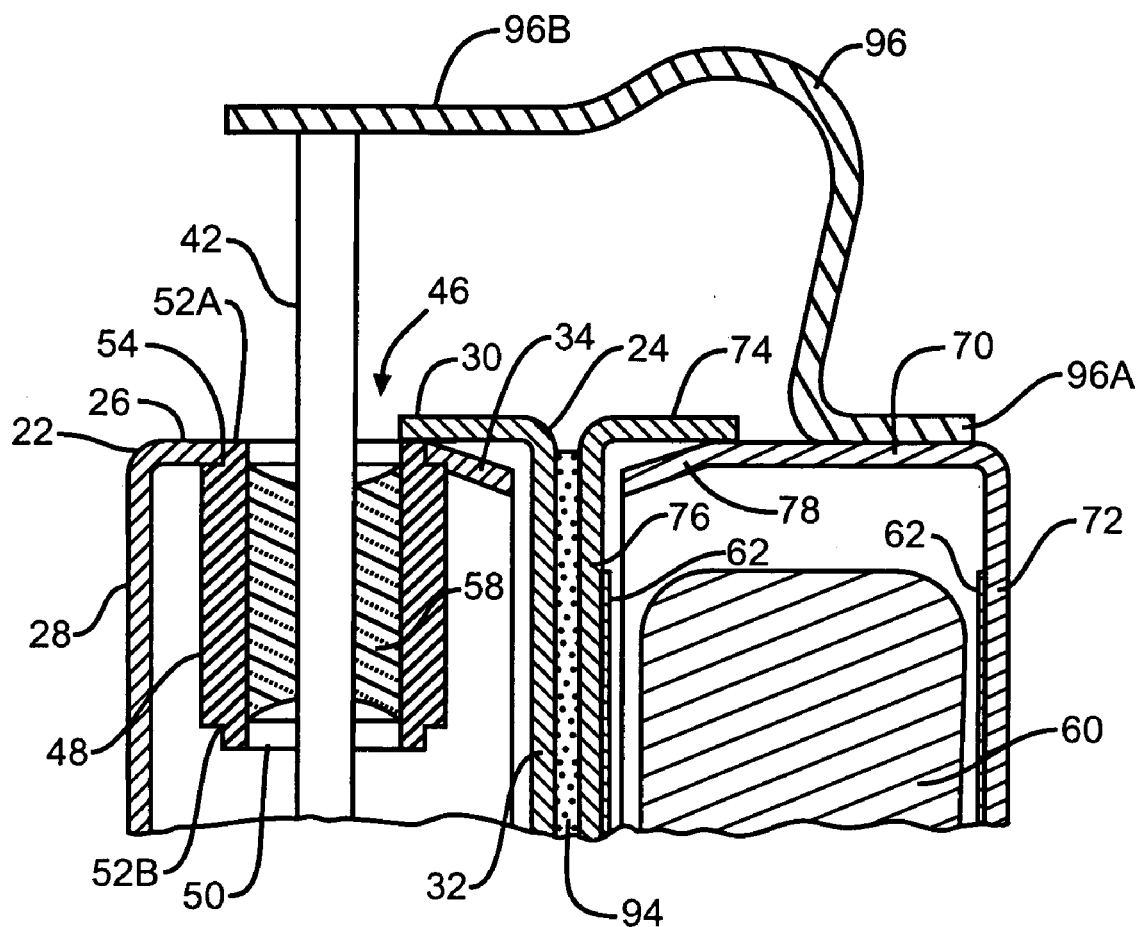
FIG. 3 is an enlarged view of the indicated area of FIG. 2.
Figure 4:
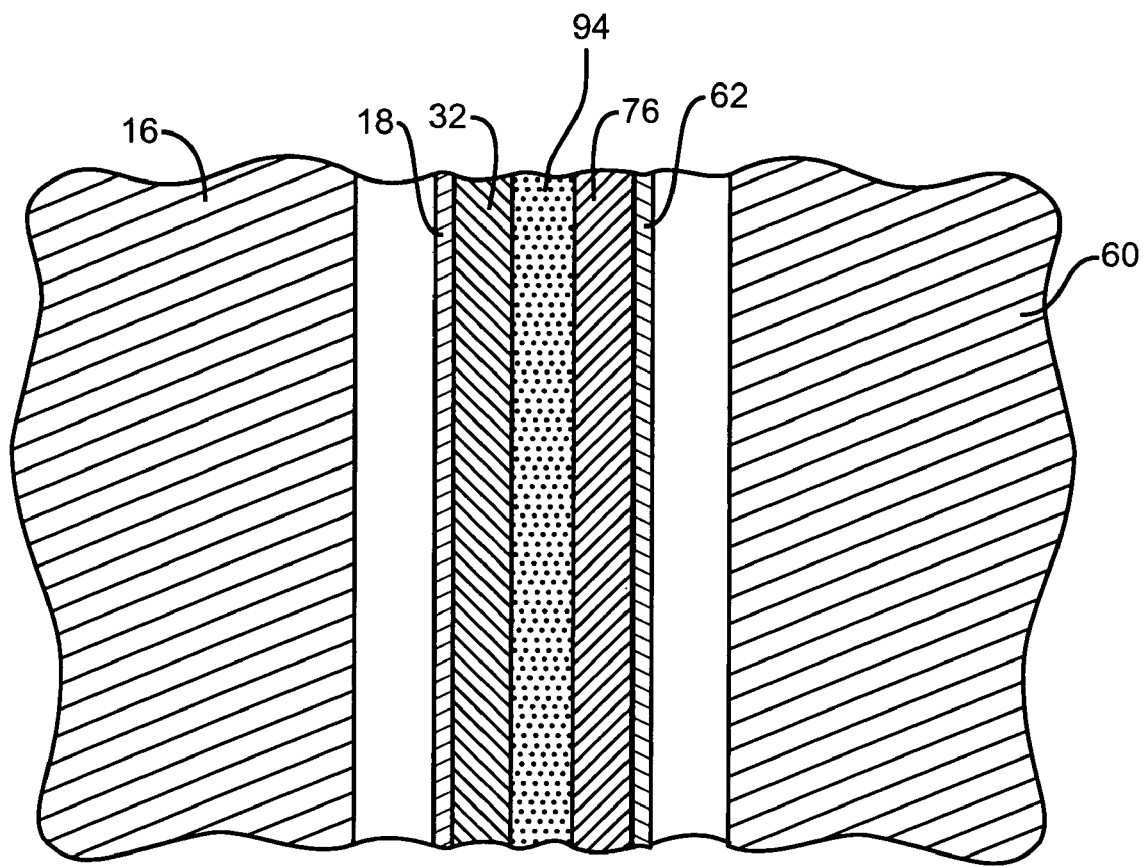
FIG. 4 is a cross-sectional view taken along line 4—4 of FIG. 2.
Figure 5:
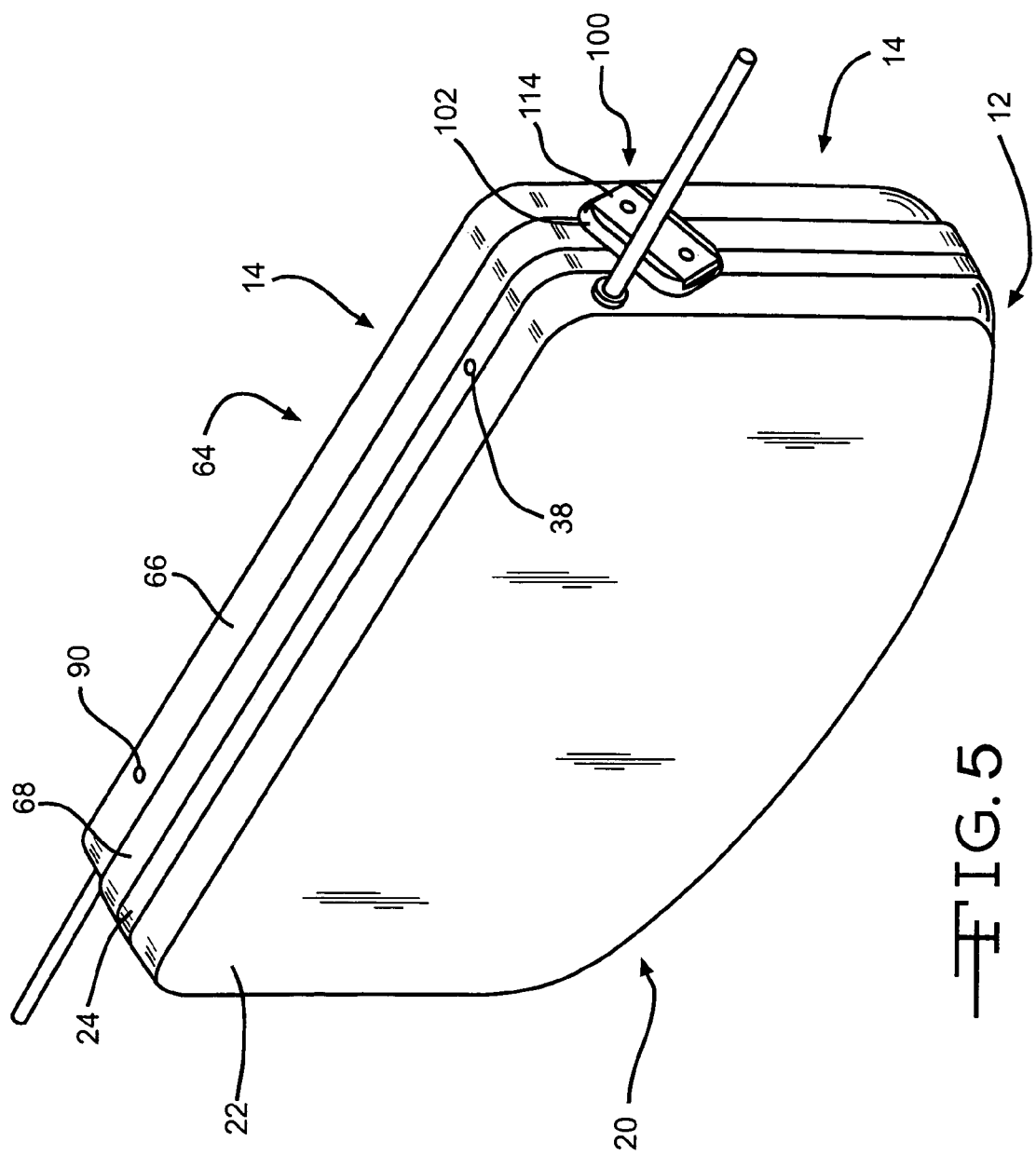
FIG. 5 is a perspective view of the side-by-side capacitors 12, 14 of FIGS. 1 to 4 connected in series with an interconnect 100 according to the present invention.

FIGS. 5 to 11 illustrate a first embodiment of a capacitor interconnect 100 according to the present invention. This interconnect is an improvement over the tab 96 and lead 42 interconnect structure described in FIGS. 1 to 4. In all other respects, the capacitors 12, 14 of this and the other present invention embodiments are the same as those described with respect to the prior art, and like structural features and designs will be given the same numerical designations.

The capacitor interconnect 100 comprises a platform 102 of an insulative thermoplastic or ceramic material having a generally oval sidewall 104 extending between an upper surface 106 and a lower surface 108. The sidewall 104 forms a pair of spaced apart rails 110 and 112 having respective upper surfaces 110A and 112A spaced above the upper surface 106 of the platform 102.

A rectangular-shaped bar 114 of a conductive material, such as of tantalum, titanium, nickel, molybdenum, niobium, cobalt, stainless steel, tungsten, platinum, palladium, gold, silver, copper, chromium, vanadium, aluminum, zirconium, hafnium, zinc, iron, and alloys thereof, comprises spaced apart right and left sidewalls 114A and 114B extending to front and back end walls 114C and 114D. These sidewalls and end walls extend to and meet with an upper surface 116 and a lower surface 118.

It is further within the scope of the invention that the conductive bar 114 can be made of any one of these materials, and alloys thereof, and then be provided with a coating on its upper surface of another one of them. This makes the conductive bar useful as a bonding pad for connection to a medical device. For example, the bar can be of nickel, aluminum, or platinum and be plated or coated with gold as a bonding pad or surface for connection to a medical device. Suitable wire bonding techniques useful with the conductive bar 114 include thermocompression ball bonding, thermosonic compressive wire bonding, ultrasonic compressive wedge bonding, thermocompression wedge bonding, stitch bonding, and tape automated bonding, among others. For more description regarding wire bonding a medical device to a conductive pad, reference is made to U.S. Pat. No. 6,626,680 to Ciurzynski et al., which is assigned to the assignee of the present invention and incorporated herein by reference.

The conductive bar 114 is provided with spaced apart openings 120 and 122 that extend through the thickness from the upper surface 116 to the lower surface 118 thereof. The platform 102 is also provided with a pair of spaced apart openings 124 and 126 that extend through the thickness from the upper surface 106 to the lower surface 108 thereof. As particularly shown in FIG. 8, a lower portion of the openings 124, 126 is beveled with a frusto-conical shape extending downwardly and outwardly toward the lower platform surface 108.

As shown in FIGS. 6 to 8, the capacitor interconnect 100 is formed by nesting the conductive bar 114 inside the rails 100 and 112 of the insulative platform 102. In this position, the lower surface 118 of the bar 114 rests on the upper surface 106 of the platform 102 and the upper surfaces 110A and 112A of the rails are coplanar with the upper surface 116 of the conductive bar 114. The right and left bar sidewalls 114A, 114B are in a closely spaced relationship with the respective rails 110, 112. The front and back end walls 114C, 114D of the conductive bar 114 are aligned with the opposed ends of the rails 110, 112. This leaves minor portions 102A and 102B at each end of the platform 102 uncovered by the bar.

Figure 9:
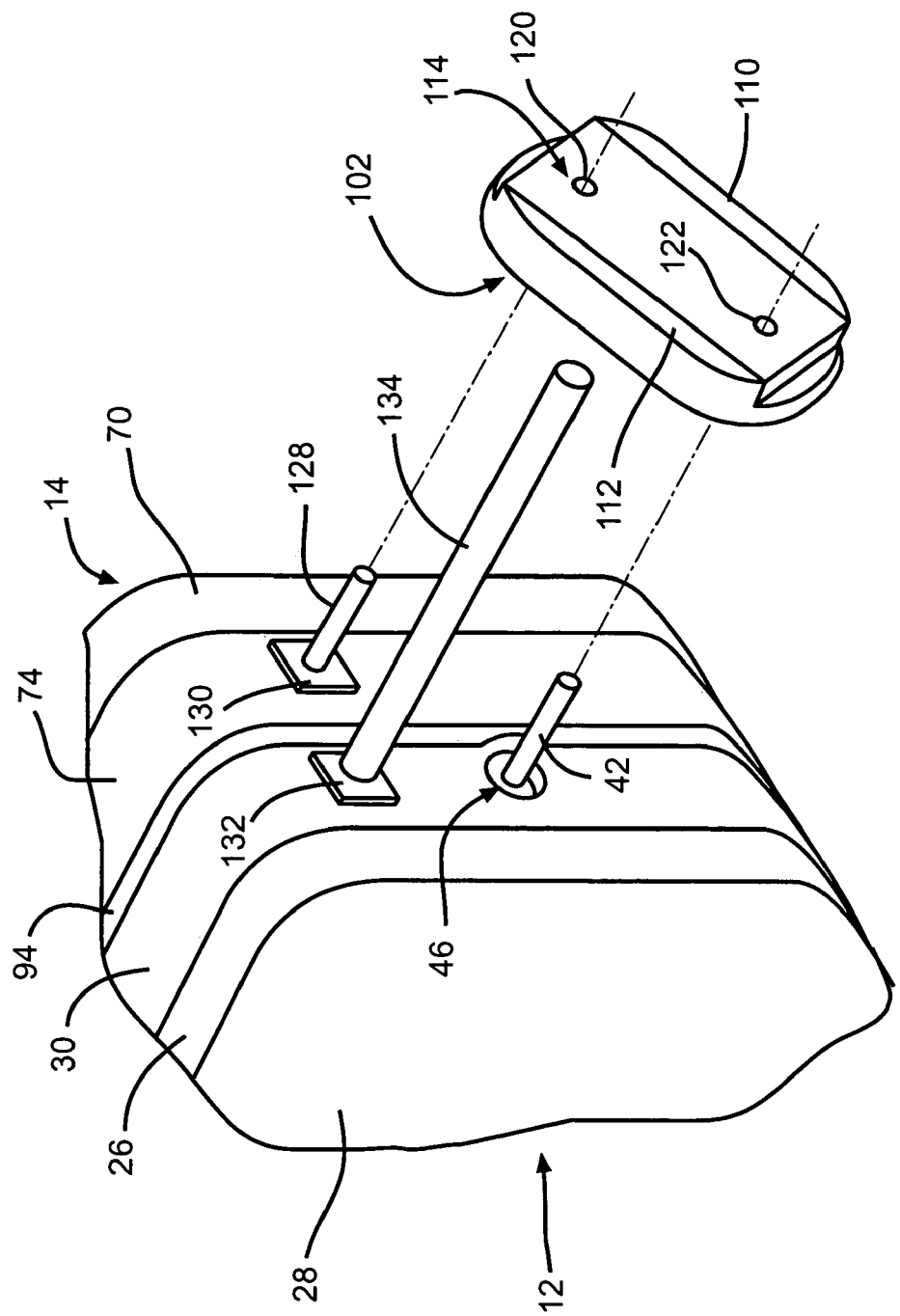
FIG. 9 is a partial perspective view of the interconnect 100 being moved onto the respective terminals 42 and 128 for the capacitors 12, 14.

As shown in FIG. 9, the connection between the capacitors 12, 14 is made by first securing a pin 128 to the surrounding sidewall 70 of the casing portion 68 for capacitor 14. In order to provide a robust connection, a flat piece of metal serving as a foot 130 is first secured to one end of the pin 128 and this assembly is then secured to the sidewall 70, such as by welding. Pin 128 now serves as the negative polarity connection for the second capacitor 14. As previously described with respect to FIGS. 1 to 4, the anode lead 42 is the positive polarity termination for the first capacitor 12.

Figure 10:
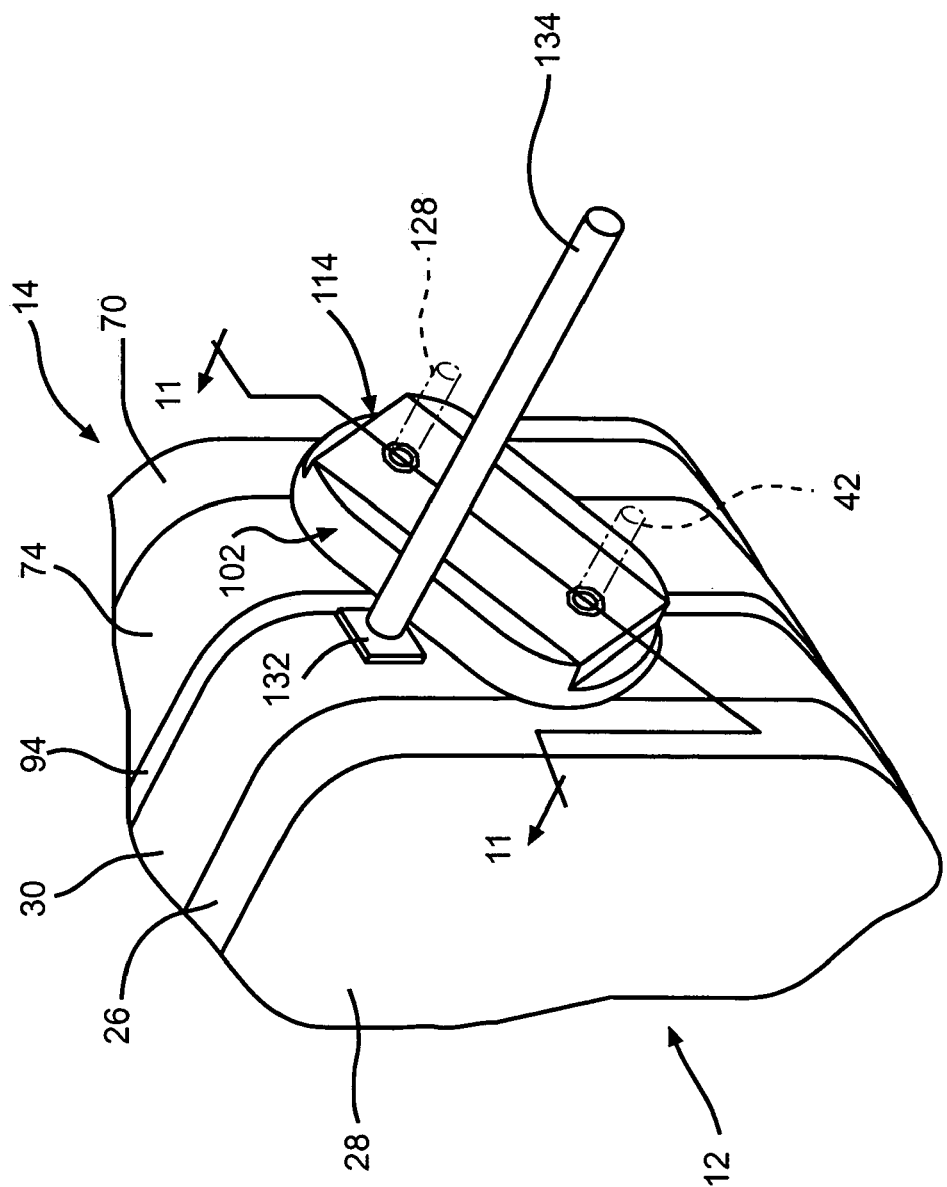
FIG. 10 is a partial perspective view of the interconnect 100 connecting the capacitors 12, 14 in FIG. 9 in series.
Figure 11:
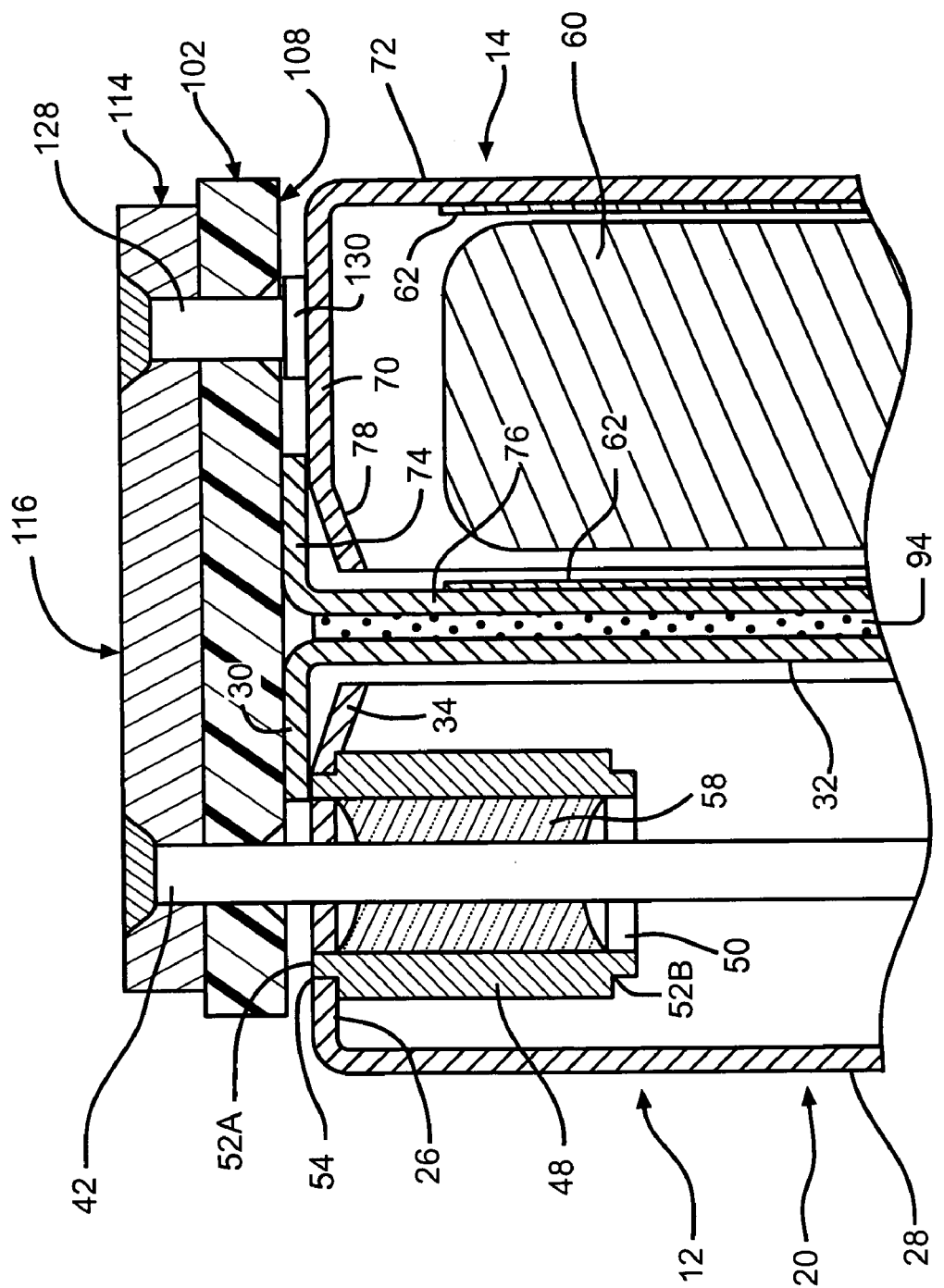
FIG. 11 is a partial cross-sectional view along line 11—11 of FIG. 10.

In order to effect a series connection between the positive polarity lead 42 and the negative polarity pin 128 of the side-by-side capacitors 12, 14, the insulative platform 102 supporting the conductive bar 114 is moved into the position shown in FIGS. 9 and 10. In that manner, the positive polarity anode lead 42 is received in the aligned openings 124 and 120 and the negative polarity pin 128 is received in the aligned openings 126 and 122 in the respective platform 102 and conductive bar 114. The beveled mouth to the platform openings 124, 126 helps with this positioning. The upper end of the lead 42 and pin 128 now extend above the upper surface 116 of the conductive bar 114. A laser (not shown) is used to sever the excess extending material from the lead and pin and to weld them to the conductive bar in a secure electrical connection, as shown in FIG. 11.

In this position, the lower surface 108 of the insulative platform 102 rests on the surrounding sidewalls 30, 74 of the casing portions 24 and 68 of the respective first and second capacitors 12, 14. The platform 102 also rests on the foot 130 of the negative polarity pin 128 at the bevel of opening 126. The capacitors, which have their respective casings electrically insulated from each other by the intermediate double-sided adhesive 94, are now serially connected to each other by the conductive bar 114 of the interconnect 100 extending from the positive polarity lead 42 of capacitor 12 to the negative polarity pin 128 of capacitor 14.

In order to make electrical connection to the series connected capacitors 12, 14, a footpad 132 secured to one end of a terminal lead 134 is secured to the casing of capacitor 14. A positive polarity pin (not shown) extends from the opposite end of the capacitor 12 electrically insulated there from by a glass-to-metal feedthrough. The series connected capacitors 12, 14 are now connectable to a load through the lead 134 and positive polarity pin.

The capacitor interconnect 100 provides many advantages over the previously described connecting tab 96 and anode lead 42 structure. Among them is that the welds of the lead 42 and pin 128 to the conductive bar 114 are easier to make, but are more robust with improved mechanical pull strength. This is without sharp edges and while occupying significantly less real estate.

Figure 13:
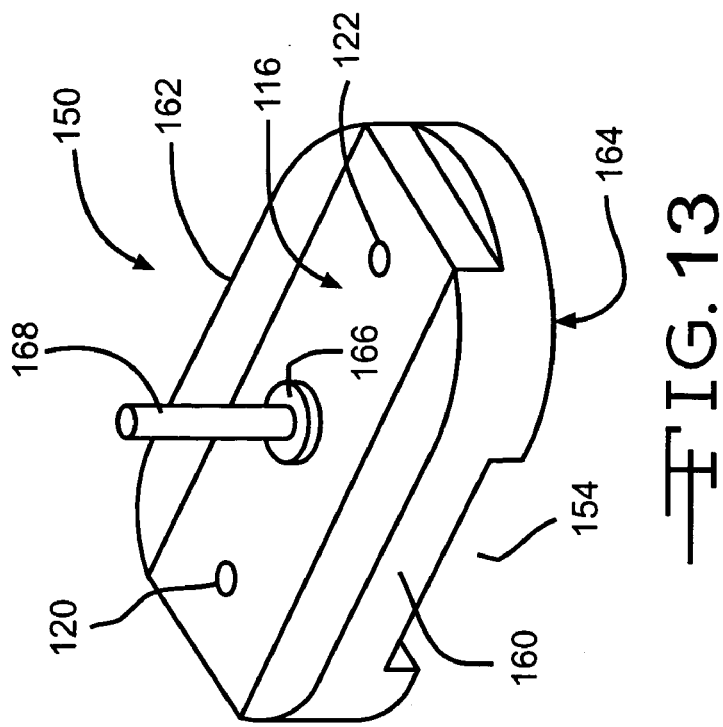
FIG. 13 is a perspective view of the assembled interconnect 150 shown in FIG. 12.
Figure 12:
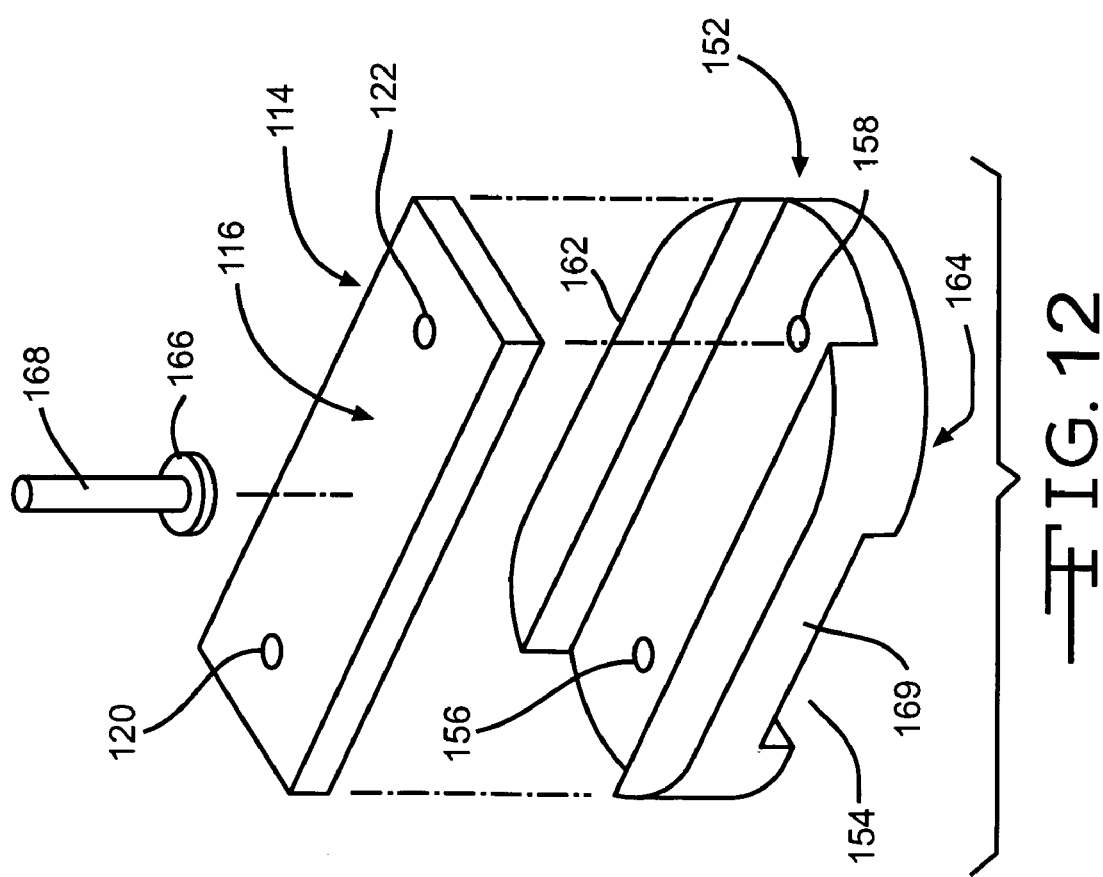
FIG. 12 is an exploded view of another embodiment of an interconnect 150 including a platform 152 and a conductive bar 114.
Figure 14:
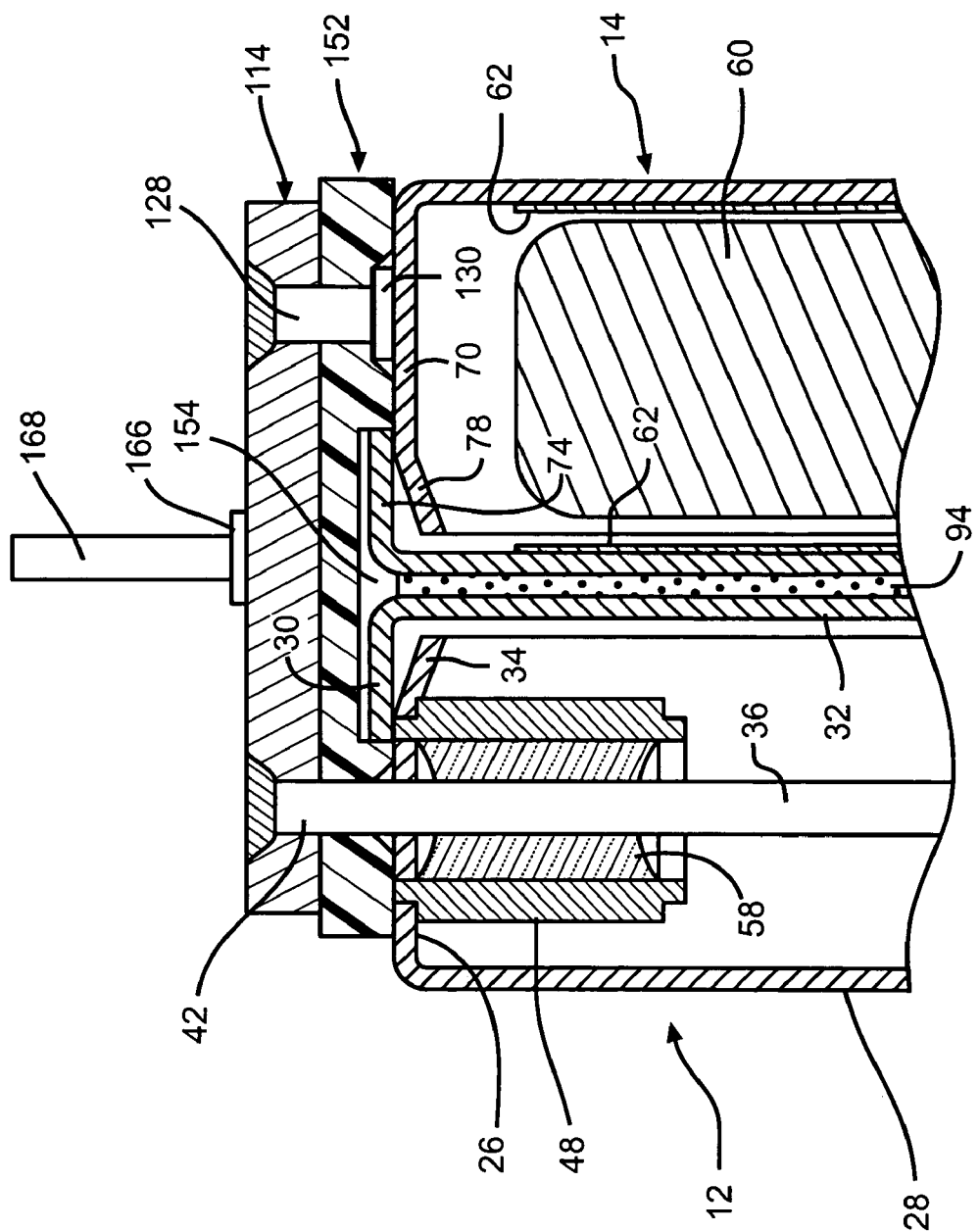
FIG. 14 is a partial cross-sectional view of the interconnect 150 connecting capacitors 12, 14 in series.

FIGS. 12 to 14 illustrate another embodiment of a capacitor interconnect 150 according to the present invention. This interconnect is similar to that of the first embodiment previously described with respect to FIGS. 5 to 11. However, the insulative platform 152 is provided with a lower surface having a recess 154 centered between the openings 156, 158. The recess extends laterally from straight sidewall portion 160 to straight sidewall portion 162 and is sized to receive and fit over the surrounding sidewalls 30, 74 of the casing portions 24, 68 of the respective capacitors 12, 14. This provides a more stable footing for the interconnect 150 with the lower surface 164 of the insulative platform 152 resting on the surrounding sidewalls 26, 70 of the casing portions 22 and 66 of the respective first and second capacitors 12, 14. The capacitors, which have their respective casings electrically insulated from each other by the intermediate double-sided adhesive 94, are now serially connected to each other by the conductive bar 114 of the interconnect 150 extending from the positive polarity lead 42 of capacitor 12 to the negative polarity pin 128 of capacitor 14.

This embodiment also shows making electrical connection to the series connected capacitors 12, 14 by securing a footpad 166/terminal lead 168 assembly to the casing of capacitor 14. The assembly is of any conductive material previously described as being useful for conductive bar 114. This is an alternative embodiment to the footpad 132/terminal lead 134 assembly shown directly connected to the casing of capacitor 14 in FIGS. 9 and 10. A positive polarity pin (not shown) extends from the opposite end of the capacitor 12 electrically insulated there from by a glass-to-metal feedthrough.

Figure 15:
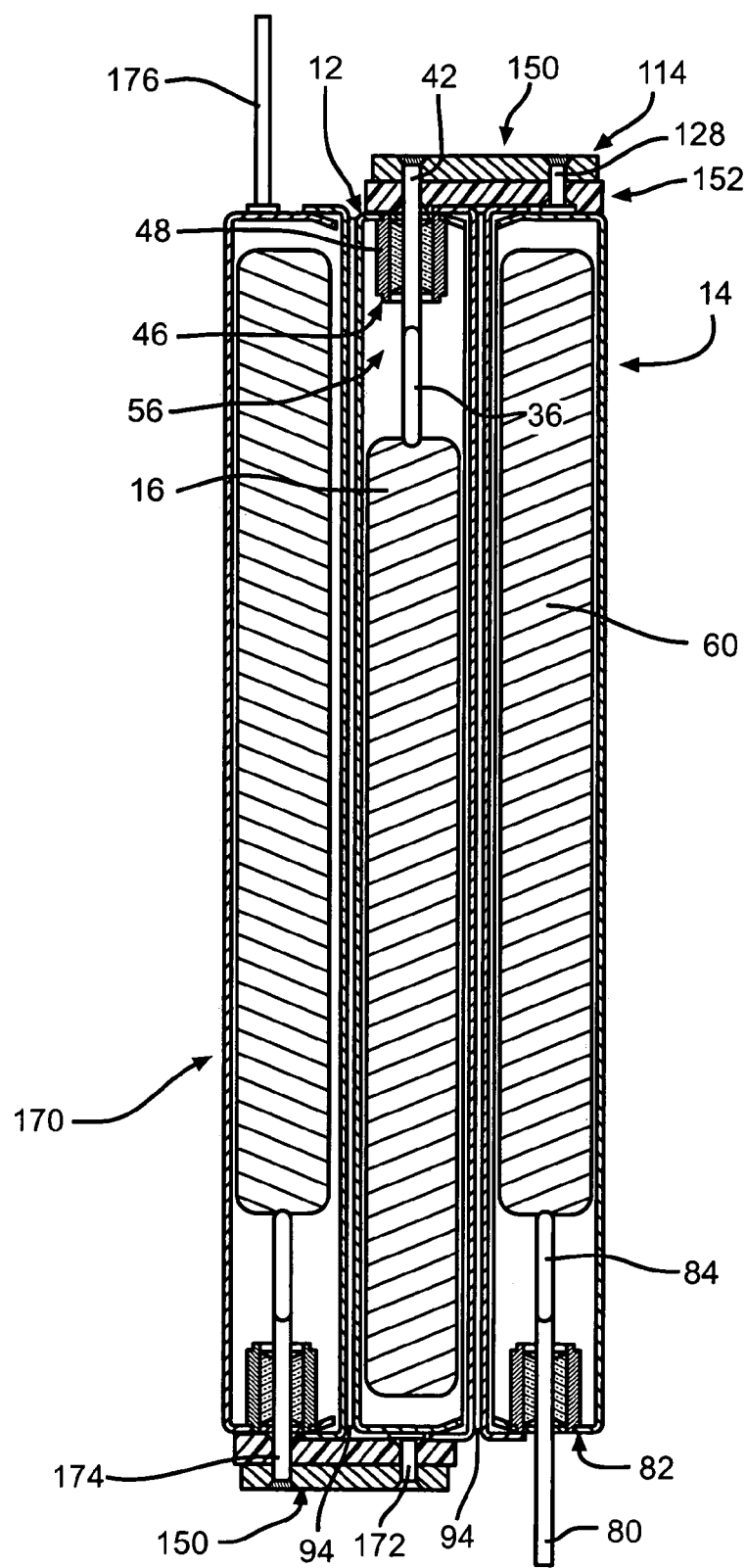
FIG. 15 is a cross-sectional view showing two of the interconnects 150 connecting three capacitors 12, 14 and 170 in series.

FIG. 15 is a cross-sectional view illustrating three side-by-side-by-side capacitors 12, 14 and 170 serially connected together using two interconnects 150. The third capacitor 170 can be either the same as or different than the capacitors 12, 14. However, for the sake of illustration, capacitor 170 is of an electrolytic type and is the same as capacitors 12, 14 in its physical structure.

The casing for capacitor 170 is electrically insulated from that of capacitor 12 by an intermediate double-sided adhesive 94. Then, the conductive bar 114 of the second interconnect 150 connects between a positive polarity pin 172 connected to the casing of capacitor 12 and the negative polarity lead 174 of capacitor 170. A negative polarity pin 176 extends from the opposite end of capacitor 170. Now, a load can be connected to the three serially connected capacitors 170, 12 and 14 by connecting to the positive polarity lead 80 of capacitor 14 and the negative polarity pin 176 of capacitor 170. Of course, those skilled in the art will recognize that if the various interconnects of the present invention can be used to connect two and three capacitors in a serial configuration, they can be used to connect four and more, as dictated by a particular application.

Figure 16:
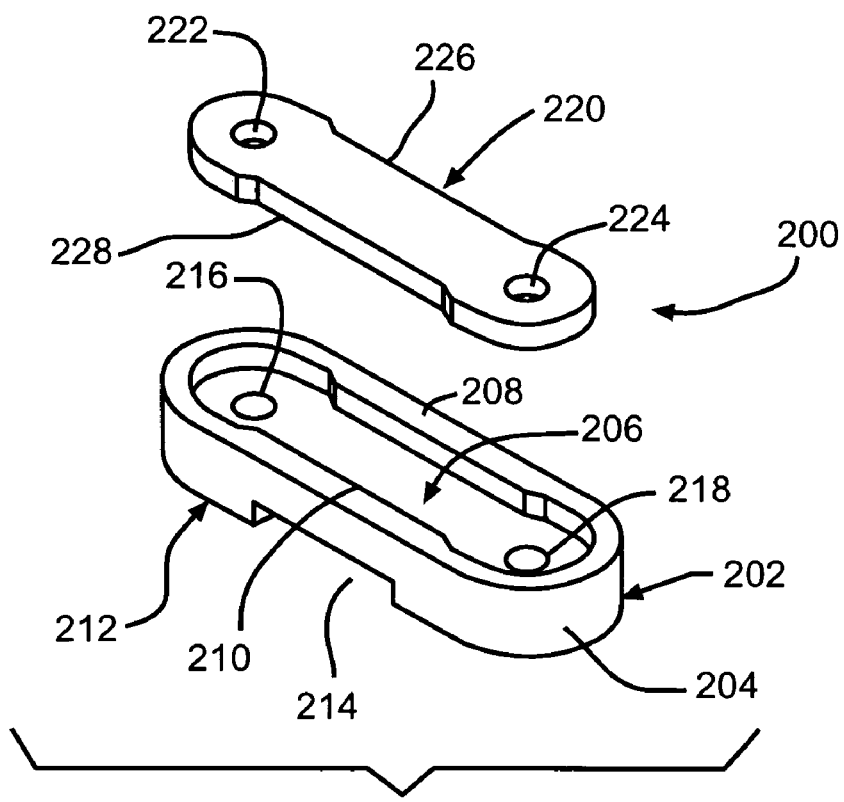
FIG. 16 is an exploded view of another embodiment of an interconnect 200 including a platform 202 and a conductive bar 220.
Figure 17:
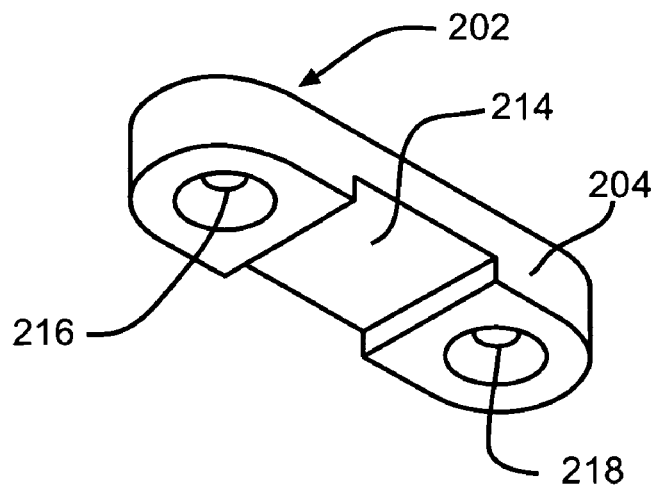
FIG. 17 is a bottom perspective view of the platform 202 for the interconnect 200 shown in FIG. 16.
Figure 18:
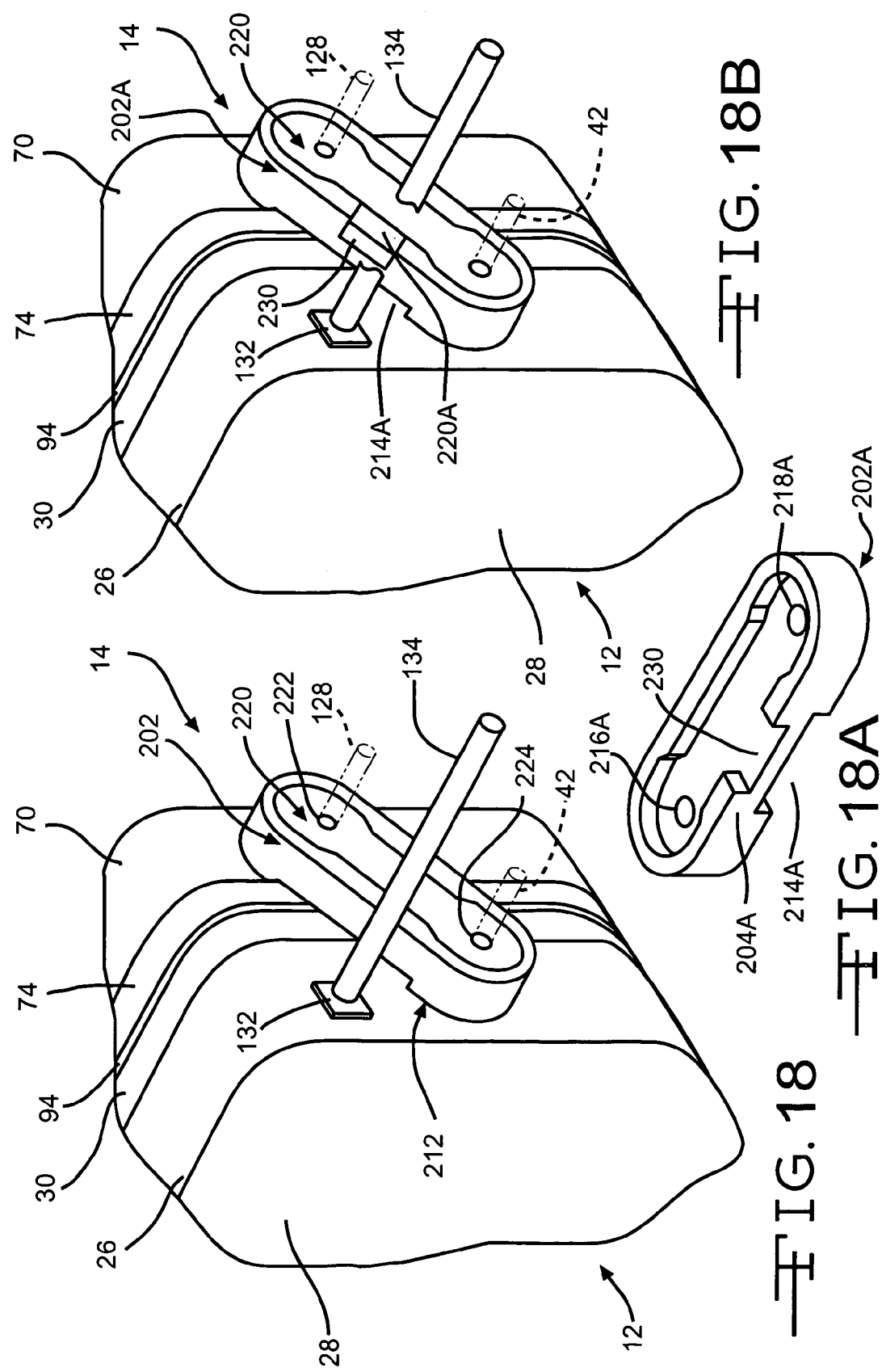
FIG. 18 is a partial perspective view of the interconnect 200 connecting the capacitors 12, 14 in series.
Figure 19:
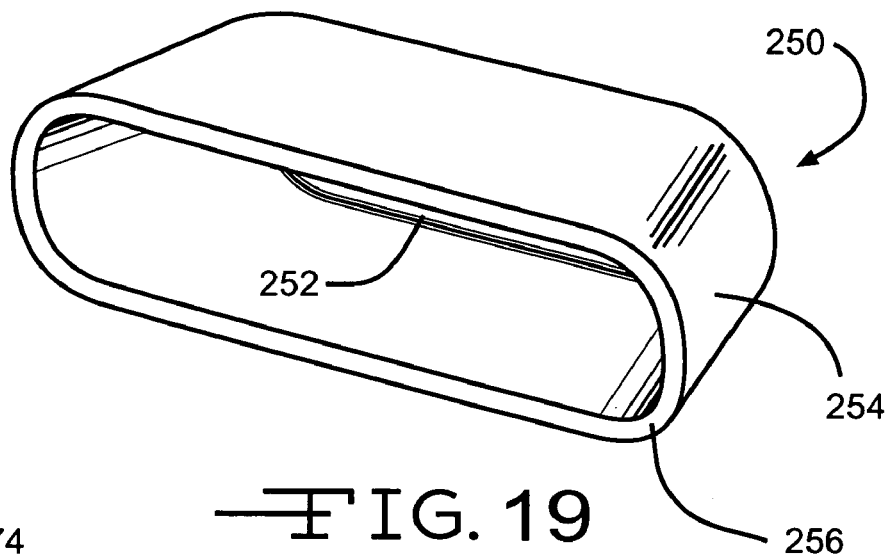
FIG. 19 is a bottom perspective view of another embodiment of an interconnect 250.
Figure 20:
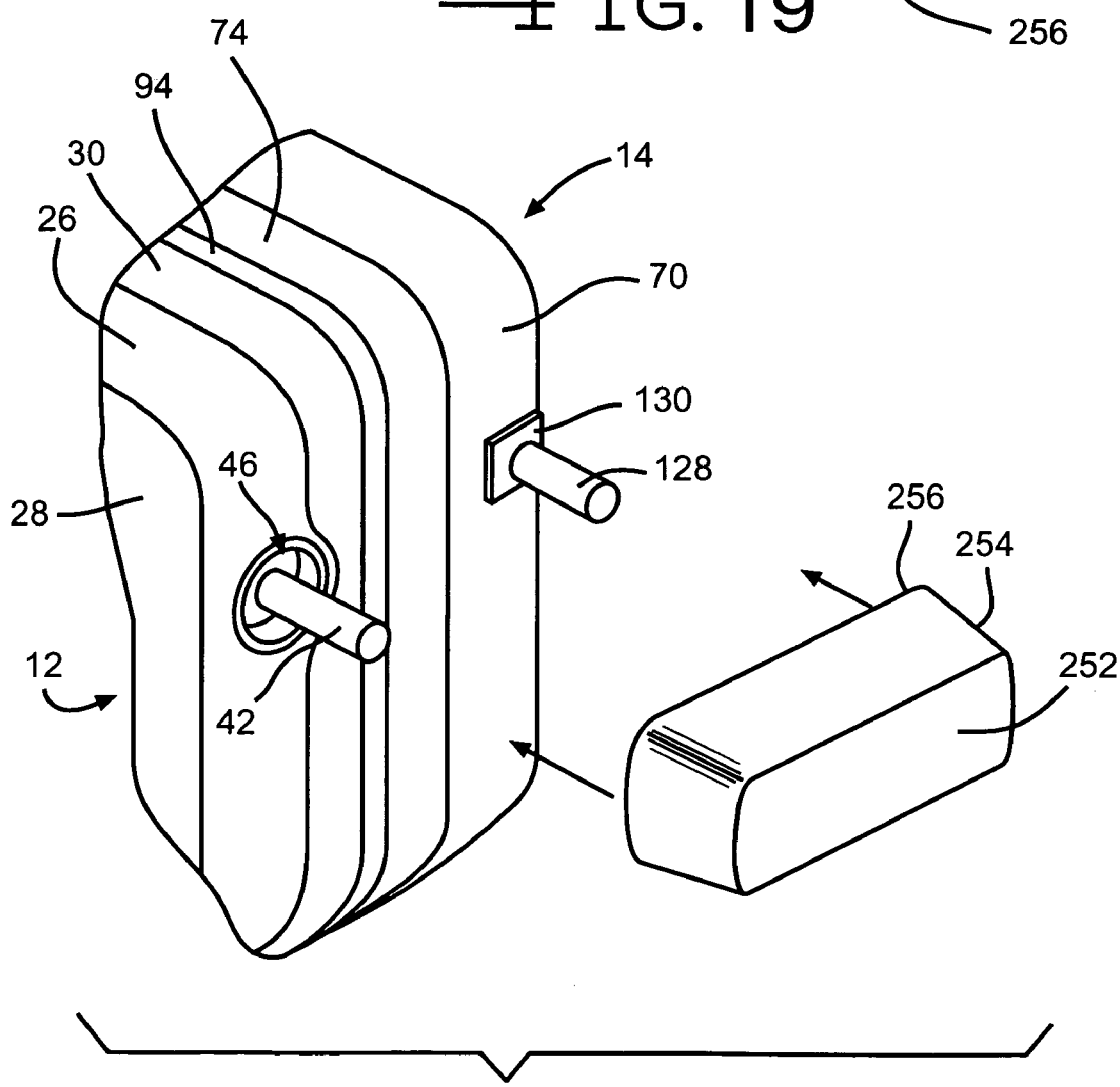
FIG. 20 is a partial perspective view of the interconnect 250 being moved onto the respective terminals 42 and 128 for the capacitors 12, 14.

FIGS. 16 to 18 illustrate another embodiment of a capacitor interconnect 200 according to the present invention. This interconnect is similar to that of the interconnect 150 previously described with respect to FIGS. 12 to 14. However, the insulative platform 202 has a surrounding oval-shaped sidewall 204 extending above an interior upper surface 206. The sidewall 204 further has opposed protruding portions 208 and 210. The lower surface 212 has a recess 214 centered between openings 216, 218 and extending laterally from opposed straight portions of sidewall 204.

The conductive bar 220 is an oval-shaped member of a similar material as bar 144 and comprises opposed openings 222 and 224 at either end with intermediate indentation portions 226 and 228. In that respect, the conductive bar 220 is received in the space enclosed by the surrounding sidewall 204 resting on the upper surface 206 of the insulative platform 202. The opposed protruding portions 208, 210 are sized to closely match the opposed indentation portions 226, 228 of the bar 220. With the conductive bar 220 nested inside the surrounding platform sidewall 204, the spaced apart openings 222 and 224 are exactly aligned with openings 216 and 218 in the insulative platform 202. Also, the upper surface of the conductive bar 220 is coplanar with the upper surface of the surrounding platform sidewall 204. Finally, the lower portions of the platform openings 216 and 218 are beveled to facilitate receiving the positive polarity anode lead 42 of capacitor 12 and the negative polarity pin 128 of capacitor 14 therein. As before, the upper end of lead 42 and pin 128 extending above the upper surface of the conductive bar 220 is removed when the conductive bar is welded to the lead and pin, such as by a laser.

In this position, the lower surface 212 of the insulative platform 202 rests on the surrounding sidewalls 30, 74 of the casing portions 24 and 68 of the respective first and second capacitors 12, 14. The insulative platform 202 also rests on the foot 130 of the negative polarity pin 128 at the bevel of opening 126. The capacitors, which have their respective casings electrically insulated from each other by the intermediate double-sided adhesive 94, are now serially connected to each other by the conductive bar 220 of the interconnect 200 extending from the positive polarity lead 42 of capacitor 12 to the negative polarity pin 128 of capacitor 14. In a similar manner as the previously described bar 114, conductive bar 220 is now a suitable structure for making a wire bond connection between the series connected capacitors 12, 14 and a medical device.

As shown in FIGS. 18A and 18B, to further facilitate a wire bond connection, the surrounding sidewall 204A of the insulative platform 202A is provided with a cutout 230 extending from the upper surface thereof to a distance spaced above the recess 214A and centered between openings 216A and 218A. With the conductive bar 220 nested inside the surrounding platform sidewall 204A, the cutout 230 exposes an edge portion 220A of the bar. The conductive bar 220 can be of any of the previously listed materials, for example nickel, aluminum, or platinum plated or coated with gold. Gold can reside on the edge 220 as well as the upper surface thereof to provide a bonding pad or surface there for connection to the medical device FIGS. 19 to 22 relate to a further embodiment of a capacitor interconnect 250 according to the present invention. Interconnect 250 is in the shape of an elongated pocket or cap of a similar material as the previously described bar 144 and having an upper wall 252 supporting a surrounding sidewall 254 extending to an oval-shaped edge 256. The sidewall 254 extends outwardly from the upper wall 252 to the edge 256 and provides an opening sized so that the cap interconnect fits over and receives the positive polarity anode lead 42 of capacitor 12 and the negative polarity pin 128 of capacitor 14. However, the sidewall 254 is of a height to prevent the cap 250 from contacting the casings of the capacitors 12, 14, as this will short them out.

Figure 21:
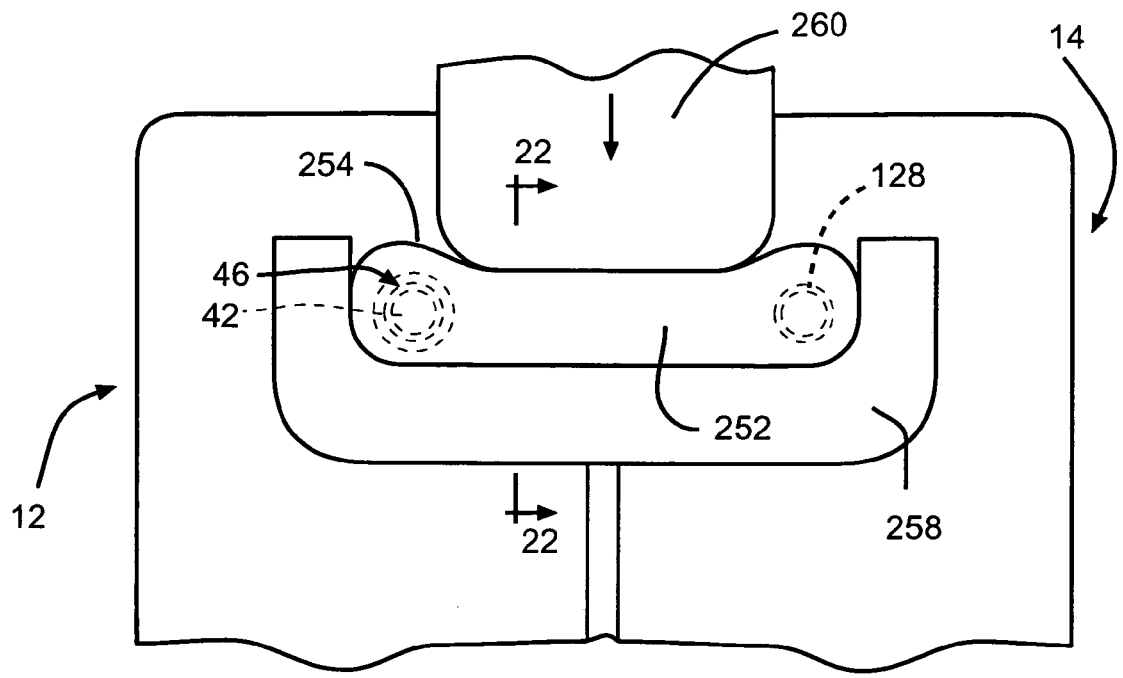
FIG. 21 is a partial top plan view showing the interconnect 250 of FIGS. 19 and 20 being deformed into locking contact with the terminals 42 and 128.
Figure 22:
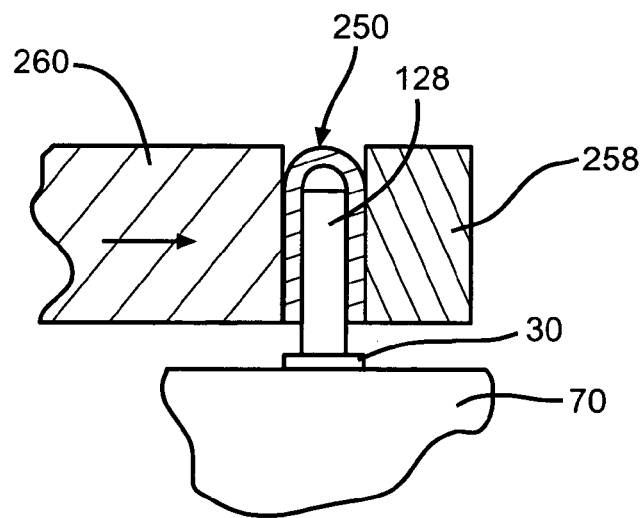
FIG. 22 is a cross-sectional view along lines 22—22 of FIG. 21.

As shown in FIG. 21, the lead 42 and pin 128 reside adjacent to the opposite ends of the cap interconnect. The electrical connector is then made by physical deformation of the cap onto the lead and pin. First, a U-shaped backing plate 258 surrounds the cap interconnect 250 on three of its "sides". A ram 260 then moves against the far portion of the surrounding sidewall 254, crushing it down and into a locking relationship with the lead 42 and pin 128. Preferably, this crushing force is sufficient to bring the opposed planar portions of the surrounding sidewall 254 into contact with each other.

Figure 25:
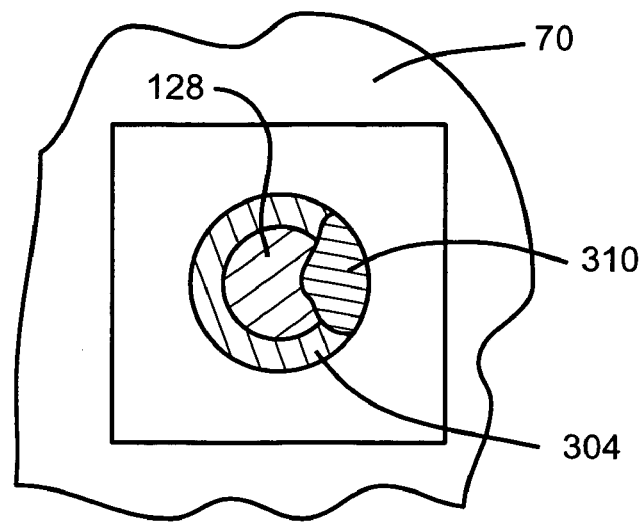
FIG. 25 is a partial cross-sectional view along lines 25—25 of FIG. 24.

FIGS. 23 to 25 illustrate another embodiment of a capacitor interconnect 300 according to the present invention. Interconnect 300 is a tubular U-shaped sleeve of a similar material as the previously described bar 144 and having a central portion 302 supporting opposed legs 304 and legs 306. The central portion 302 is of a length such that the cylindrically shaped openings in legs 304, 306 snuggly receive the positive polarity anode lead 42 of capacitor 12 and the negative polarity pin 128 of capacitor 14 in a co-axial relationship thereof. Welding the legs 304, 306 to the lead 42 and pin 128, such as by using a laser 308 makes the electrical connection. A weldment 310 at each leg then effects the connection.

Figure 26:
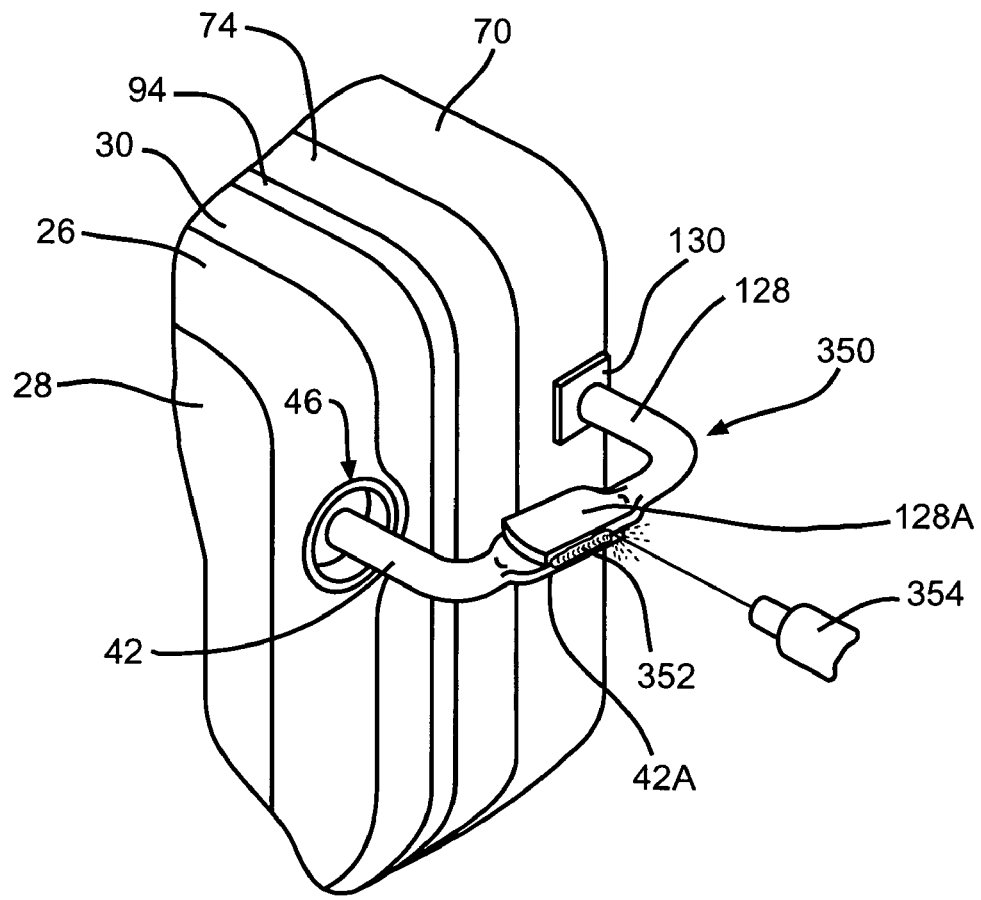
FIG. 26 is a partial perspective view of another embodiment of an interconnect 350 showing distal portions 42A and 128A of the respective lead and conductive pin provided in a side-by-side lap joint relationship and being welded together to connect the capacitors 12, 14 in series.

FIG. 26 illustrates a further embodiment of a capacitor interconnect 350 according to the present invention. Interconnect 350 comprises the lead 42 and pin 128 having extending portions that were previously aligned in a side-by-side orientation and then subjected to a clamping force. This provides lead 42 having a distal portion 42A lapping a distal portion 128A of terminal pin 128. The distal portions 42A and 128A provided in the side-by-side lap joint relationship are then secured together such as by a weldment 352 created by laser 354.

Figure 27:
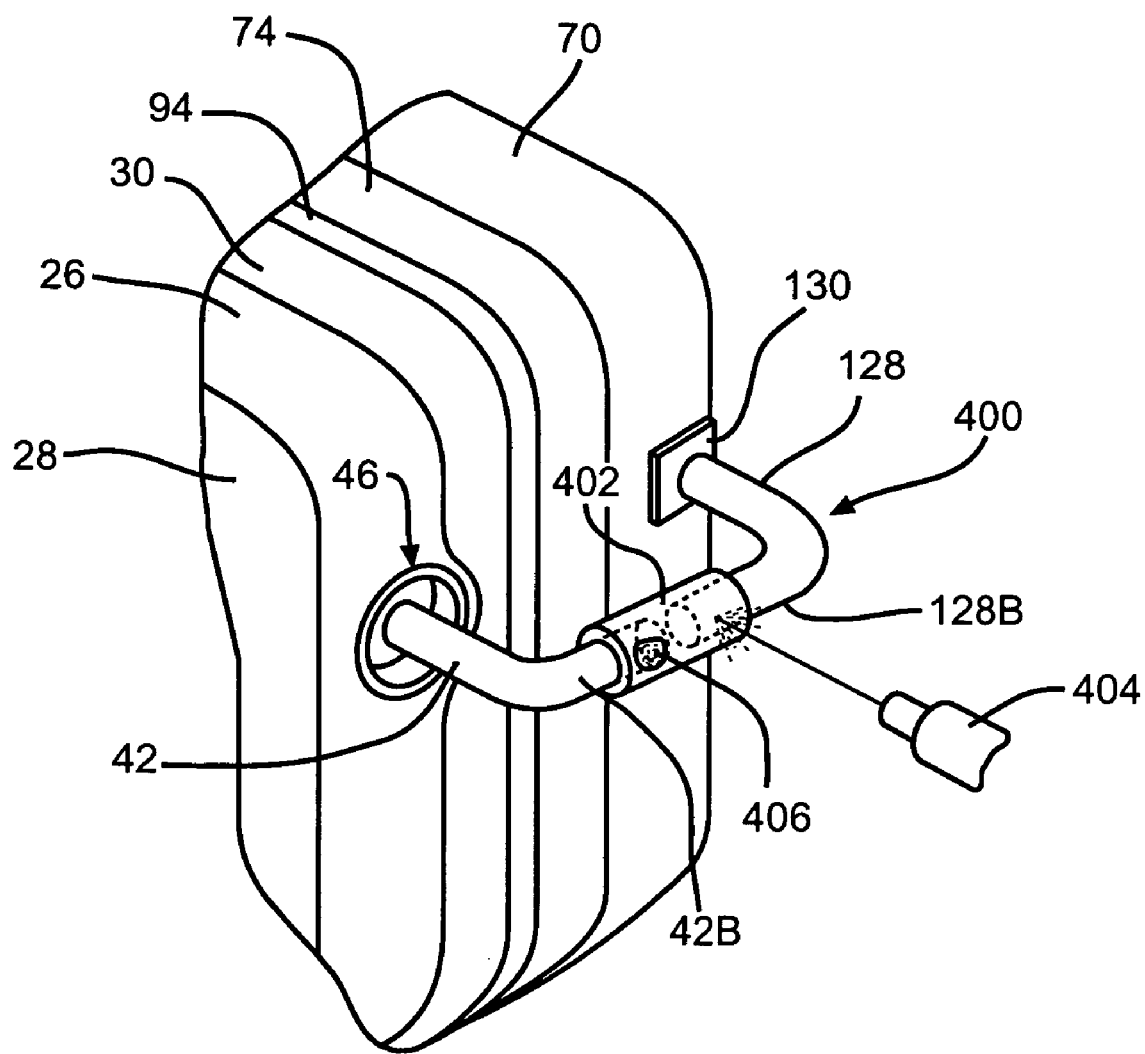
FIG. 27 is a partial perspective view of another embodiment of an interconnect 400 for connecting capacitors 12, 14 in series.

FIG. 27 illustrates a further embodiment of a capacitor interconnect 400 according to the present invention. Interconnect 400 comprises the lead 42 and pin 128 having respective L-shaped distal portions 32B and 128B that are secured together by an intermediate sleeve 402. This is done by first fitting one end of the sleeve over one of lead 42 and pin 128, for example the distal portion 42B of lead. The double-sided adhesive layer 94 has previously been contacted to the major face 32 of the casing portion 24 for capacitor 12. Capacitor 14 is then moved into place putting the capacitors 12, 14 in a side-by-side relationship with the face wall 76 of casing portion 68 contacting the other side of the adhesive 94. As this occurs, the distal portion 128B of pin 128 is fitted into the other end of sleeve 402. A laser 404 is then used to secure the sleeve 402 to the distal portions 42B and 128B of the lead and pin. A weldment 406 is shown connecting the distal lead portion 42B to the sleeve 402.

Thus, according to the present invention, adjacent capacitors are connectable in series by connecting the anode terminal lead from one to the casing of another. The anode terminal lead can be connected to the next capacitor's casing by any one of the interconnects 100, 150, 200, 250, 300, 350 and 400. That way, any number of capacitors is serially connected together to increase the delivered capacity of the assembly. This is particularly important in advanced implantable medial devices, such as cardiac defibrillators, where delivered capacity coupled with reduced package volume is paramount in the minds of the design engineers.

It is appreciated that the various modifications to the inventive concepts described herein may be apparent to those of ordinary skill in the art without departing from the spirit and scope of the present invention as defined by the appended claims.

What is claimed is:

1. A capacitor assembly, which comprises:
    a) a first capacitor having a first anode and a first cathode operatively associated with each other by an electrolyte contained inside a first casing, wherein one of the first anode and the first cathode is connected to a first lead extending outside the first casing and insulated therefrom and the other of the first anode and the first cathode is connected to the first casing and a first terminal pin for the first capacitor;
    b) a second capacitor having a second anode and a second cathode operatively associated with each other by an electrolyte contained inside a second casing, wherein the one of the second anode and the second cathode that is of the opposite polarity as that of the first anode and the first cathode connected to the first lead is connected to the second casing and the other of the second anode and the second cathode is connected to a second lead extending outside the second casing and insulated therefrom; and
    c) a first connector providing electrical connection from the first terminal pin of the first capacitor to the second lead of the second capacitor to thereby electrically connect the first and second capacitors in series.

2. The capacitor assembly of claim 1 wherein the first connector is a conductive member having at least one opening that receives the first terminal pin and the second lead.

3. The capacitor assembly of claim 2 wherein the first connector has spaced apart first and second openings that receive the first terminal pin and the second lead.

4. The capacitor assembly of claim 1 wherein the first connector is selected from the group consisting of a bar, a sleeve, and a cap.

5. The capacitor assembly of claim 1 wherein the first connector comprises a first distal portion of the first terminal pin and a second distal portion of the second lead secured together in a lap joint relationship.

6. The capacitor assembly of claim 1 wherein the first connector is a bar supported on a non-conductive platform resting on the first and second casings.

7. The capacitor assembly of claim 1 wherein the first and second series connected capacitors are positioned side-by-side with an adhesive disposed therebetween.

8. The capacitor assembly of claim 1 wherein the first casing comprises first and second casing portions, the first casing portion comprising a first face wall extending to a surrounding first sidewall and the second casing portion comprises a second face wall extending to a surrounding second sidewall with the first sidewall sealed to the second sidewall and wherein the second casing comprises third and fourth casing portions, the third casing portion comprising a third face wall extending to a surrounding third sidewall and the fourth casing portion comprising a fourth face wall extending to a surrounding fourth sidewall with the third sidewall sealed to the fourth sidewall, and wherein the first and second series connected capacitors are positioned with the first face wall proximate to and aligned with the third face wall.

9. The capacitor assembly of claim 8 wherein the first connector is a bar supported on a non-conductive platform resting on the first and second casings and wherein the non-conductive member has a recess that fits over the first and third surrounding sidewalls.

10. The capacitor assembly of claim 1 wherein a second terminal pin is secured to the second casing and wherein a third capacitor comprises a third anode and a third cathode operatively associated with each other by an electrolyte contained inside a third casing, wherein the one of the third anode and the third cathode that is of the opposite polarity as that of the second anode and the second cathode connected to the second casing is connected to a third lead extending outside the third casing and insulated therefrom and the other of the third anode and the third cathode is connected to the third casing, and wherein a second connector provides electrical connection from the second terminal pin of the second capacitor to the third lead to thereby electrically connect the second and third capacitors in series.

11. The capacitor assembly of claim 1 wherein the first and second capacitors are of either an electrolytic or an electrochemical type.

12. A method for providing a first capacitor and a second capacitor electrically connected to each other in series, comprising the steps of:
   a) providing a first capacitor having a first anode and a first cathode operatively associated with each other by an electrolyte contained inside a first casing, and connecting one of the first anode and the first cathode to a first lead extending outside the first casing and insulated therefrom and the other of the first anode and the first cathode to the first casing and a first terminal pin for the first capacitor;
   b) providing a second capacitor having a second anode and a second cathode operatively associated with each other by an electrolyte contained inside a second casing, and connecting the one of the second anode and the second cathode that is of the opposite polarity as that of the first anode and the first cathode connected to the first lead to the second casing and the other of the second anode and the second cathode to a second lead extending outside the second casing and insulated therefrom; and
   c) providing a first connector electrically connecting the first terminal pin of the first capacitor to the second lead of the second capacitor to thereby electrically connect the first and second capacitors in series.

13. The method of claim 12 including providing the first connector as a conductive member having at least one opening that receives the first terminal pin and the second lead.

14. The method of claim 13 including providing the first connector having spaced apart first and second openings receiving the first terminal pin and the second lead.

15. The method of claim 12 including selecting the first connector from the group consisting of a bar, a sleeve, and a cap.

16. The method of claim 12 including securing a lap joint relationship between a first distal portion of the first terminal pin and a second distal portion of the second lead to provide the first connector.

17. The method of claim 12 including providing the first connector as a bar supported on a non-conductive platform resting on the first and second casings.

18. The method of claim 12 including providing the first casing comprising first and second casing portions, the first casing portion comprising a first face wall extending to a surrounding first sidewall and the second casing portion comprises a second face wall extending to a surrounding second sidewall with the first sidewall sealed to the second sidewall and providing the second casing comprising third and fourth casing portions, the third casing portion comprising a third face wall extending to a surrounding third sidewall and the fourth casing portion comprising a fourth face wall extending to a surrounding fourth sidewall with the third sidewall sealed to the fourth sidewall, and positioning the first and second series connected capacitors with the first face wall proximate to and aligned with the third face wall.

19. The method of claim 18 including providing the first connector as a bar supported on a non-conductive platform resting on the first and second casings with the non-conductive member having a recess fitting over the first and third surrounding sidewalls.

20. A method for connecting a capacitor assembly to a medical device, comprising the steps of:
   a) providing a first capacitor having a first anode and a first cathode operatively associated with each other by an electrolyte contained inside a first casing, and connecting one of the first anode and the first cathode to a first lead extending outside the first casing and insulated therefrom and the other of the first anode and the first cathode to the first casing and a first terminal pin for the first capacitor;
   b) providing a second capacitor having a second anode and a second cathode operatively associated with each other by an electrolyte contained inside a second casing, and connecting the one of the second anode and the second cathode that is of the opposite polarity as that of the first anode and the first cathode connected to the first lead to the second casing and the other of the second anode and the second cathode to a second lead extending outside the second casing and insulated therefrom;
   c) providing a first connector as a bar supported on a non-conductive platform resting on the first and second casings and electrically connecting the first terminal pin of the first capacitor to the second lead of the second capacitor to thereby electrically connect the first and second capacitors in series; and
   d) bonding a wire from the medical device to an exposed upper or edge surface of the conductive bar.

* * * * *